United States Patent
Abe et al.

(10) Patent No.: US 10,408,903 B2
(45) Date of Patent: Sep. 10, 2019

(54) SHIMMING SYSTEM AND SHIMMING METHOD INCLUDING A SENSOR UNIT HAVING A PLURALY OF MAGNETIC FIELD SENSORS

(71) Applicant: HITACHI, LTD., Tokyo (JP)

(72) Inventors: Mitsushi Abe, Tokyo (JP); Kenji Sakakibara, Tokyo (JP); Takuya Fujikawa, Tokyo (JP); Hikaru Hanada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 159 days.

(21) Appl. No.: 15/550,160

(22) PCT Filed: Feb. 19, 2016

(86) PCT No.: PCT/JP2016/054879
§ 371 (c)(1),
(2) Date: Aug. 10, 2017

(87) PCT Pub. No.: WO2016/133204
PCT Pub. Date: Aug. 25, 2016

(65) Prior Publication Data
US 2018/0246180 A1    Aug. 30, 2018

(30) Foreign Application Priority Data

Feb. 20, 2015  (JP) ................................. 2015-031254

(51) Int. Cl.
*G01R 33/3875* (2006.01)
*A61B 5/055* (2006.01)
(Continued)

(52) U.S. Cl.
CPC .......... *G01R 33/3875* (2013.01); *A61B 5/055* (2013.01); *G01R 33/243* (2013.01); *G01R 33/3873* (2013.01)

(58) Field of Classification Search
CPC .... G01R 33/3875; G01R 33/243; A61B 5/055
See application file for complete search history.

(56) References Cited

U.S. PATENT DOCUMENTS 4,812,765 A    3/1989  Aubert
2002/0057155 A1    5/2002  Schauwecker et al.
(Continued)

FOREIGN PATENT DOCUMENTS

JP    2004073660 A    3/2004
JP    2011062274 A    3/2011
(Continued)

OTHER PUBLICATIONS

International Search Report of PCT/JP2016/054879 dated May 24, 2016.

*Primary Examiner* — G. M. A Hyder
(74) *Attorney, Agent, or Firm* — Mattingly & Malur, PC

(57) ABSTRACT

The present invention provides a shimming method in which an electric current surface that is virtually placed so as to surround a measurement position is assumed from a magnetic field measurement value, in which an electric current distribution that reproduces a measurement magnetic field is reproduced through an electric current potential, and in which the reproduced magnetic field distribution is used. A magnetic moment or an electric current distribution that reproduces a magnetic field distribution obtained by a magnetic field measurement device is estimated on a predetermined closed surface, and, from the estimated magnetic moment or electric current distribution, a magnetic field distribution of an arbitrary point that exists in the closed surface is estimated. Then, on the basis of the estimated magnetic field distribution, a shim magnetic body distribution that produces a correction magnetic field for correcting the magnetic field distribution at the arbitrary point is output.

11 Claims, 17 Drawing Sheets

(51) Int. Cl.
*G01R 33/24* (2006.01)
*G01R 33/3873* (2006.01)

(56) References Cited

U.S. PATENT DOCUMENTS

| | | | | |
|---|---|---|---|---|
| 2007/0229077 A1* | 10/2007 | Punzo | ............... | G01R 33/3802 |
| | | | | 324/320 |
| 2011/0057655 A1 | 3/2011 | Ando et al. | | |
| 2011/0089943 A1* | 4/2011 | Abe | ............... | G01R 33/3873 |
| | | | | 324/301 |
| 2012/0268119 A1* | 10/2012 | Abe | ............... | G01R 33/3873 |
| | | | | 324/307 |
| 2014/0009152 A1 | 1/2014 | Sakakibara | | |
| 2015/0338475 A1* | 11/2015 | Overweg | ............. | G01R 33/243 |
| | | | | 324/309 |
| 2018/0031650 A1* | 2/2018 | Abe | ............... | G01R 33/3873 |

FOREIGN PATENT DOCUMENTS

| | | |
|---|---|---|
| JP | 2014004169 | 1/2014 |
| WO | 2015005109 A1 | 1/2015 |

\* cited by examiner

[Fig. 1]
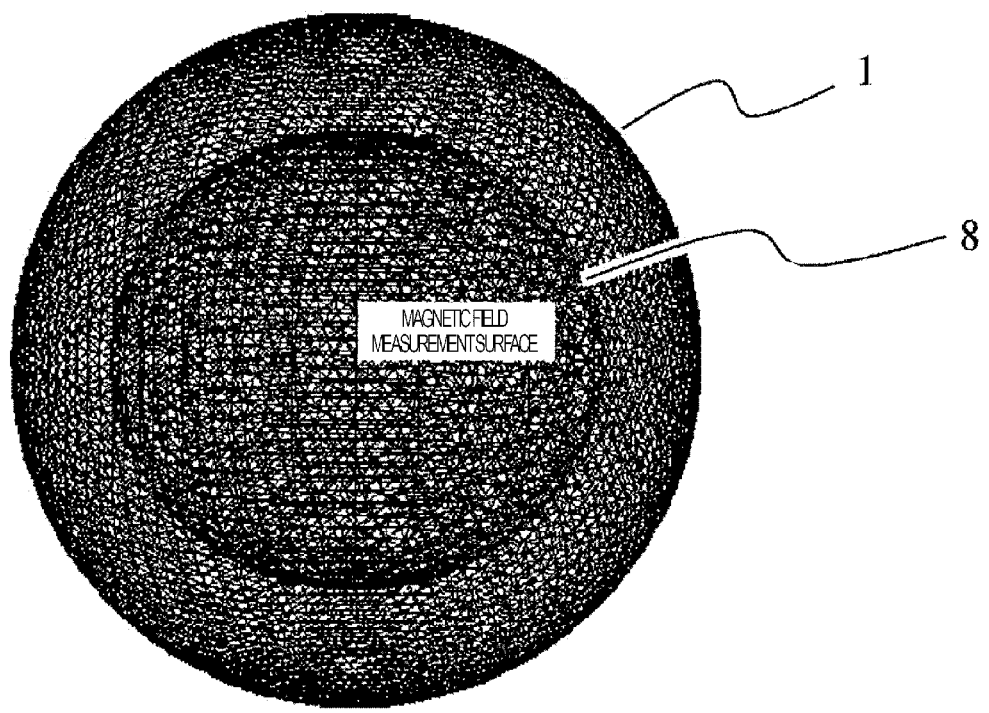

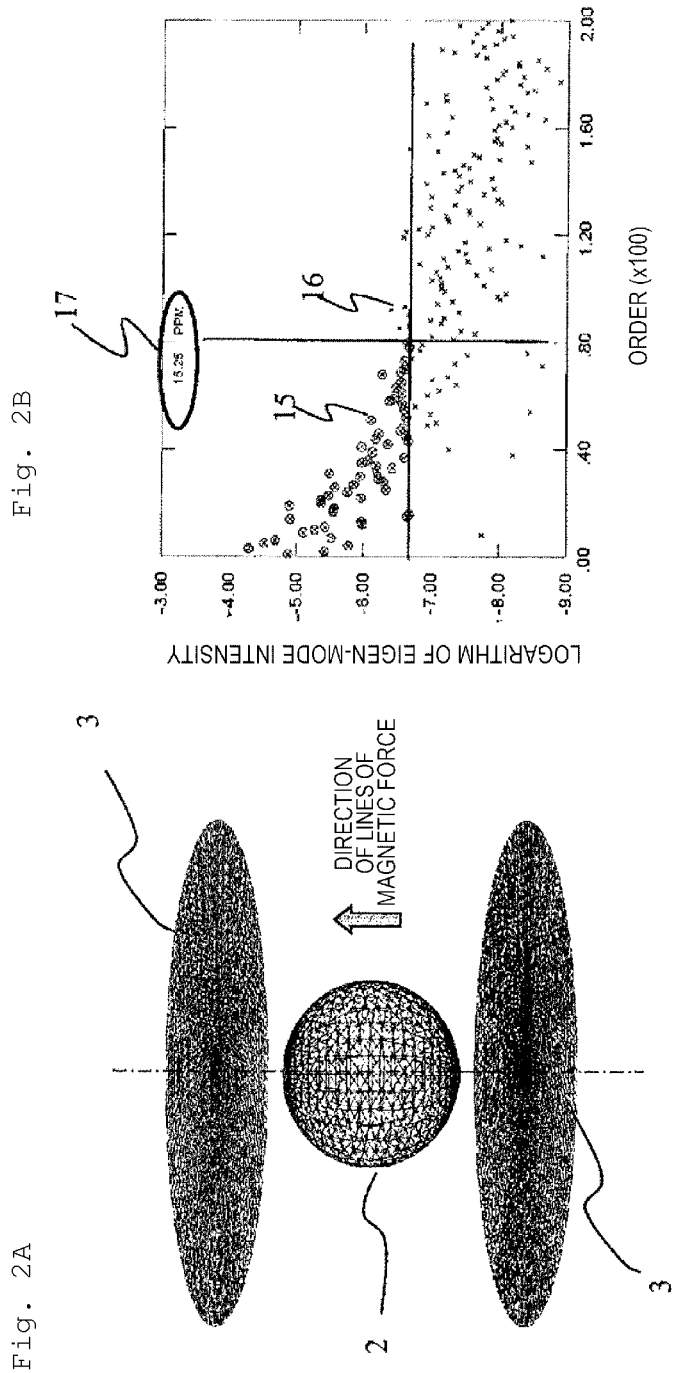

[Fig. 3]
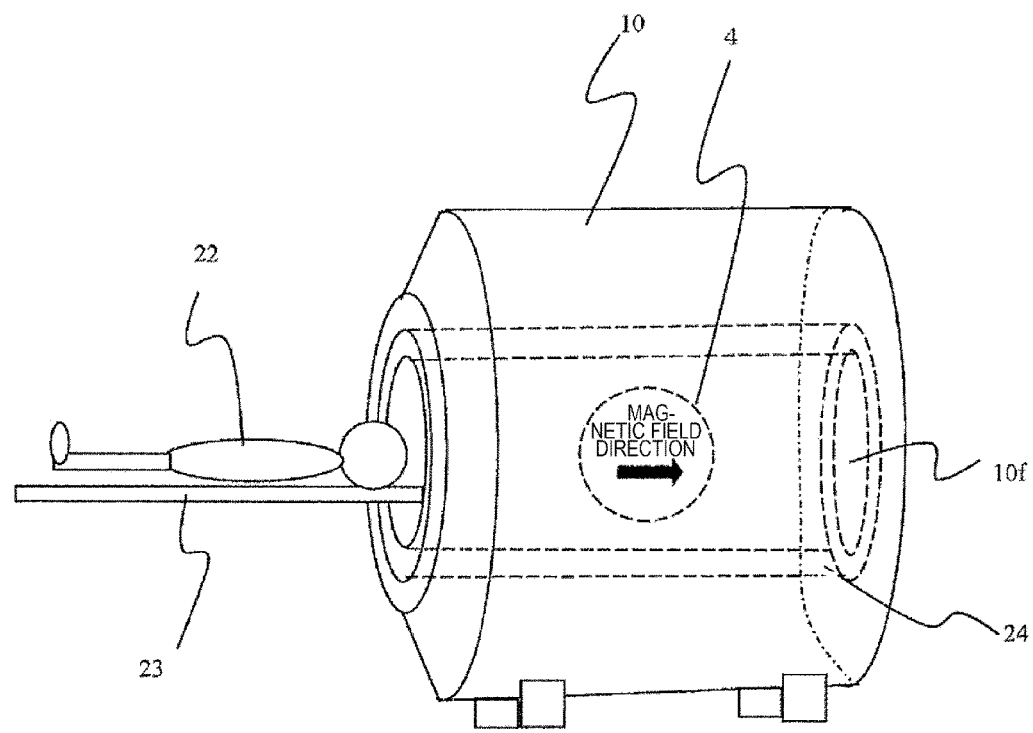

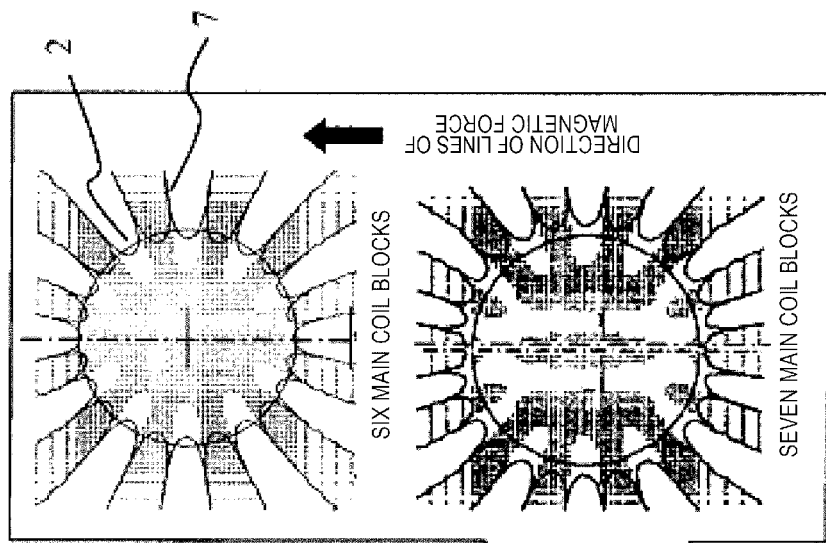
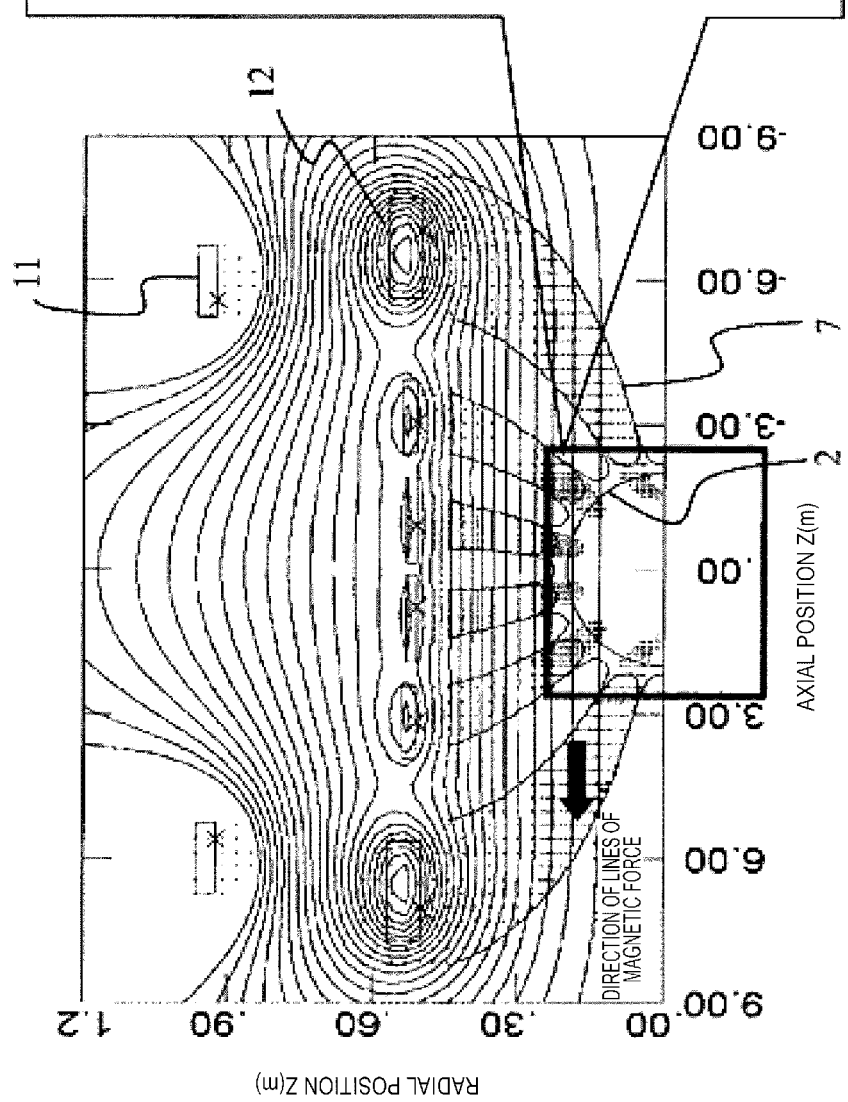
Fig. 4A
Fig. 4B

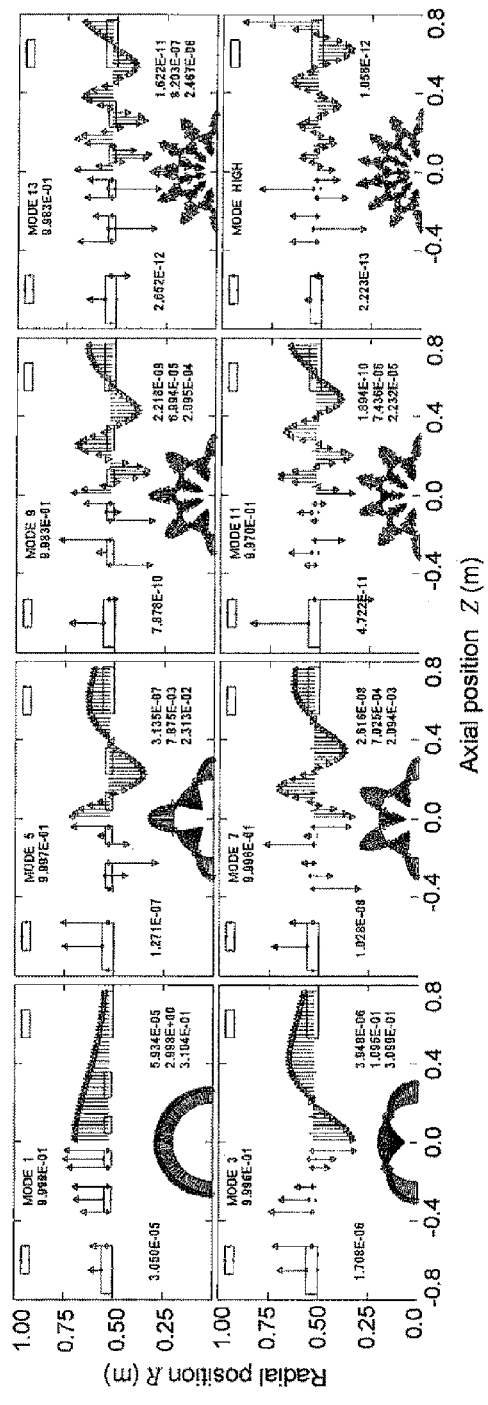
[Fig. 5]

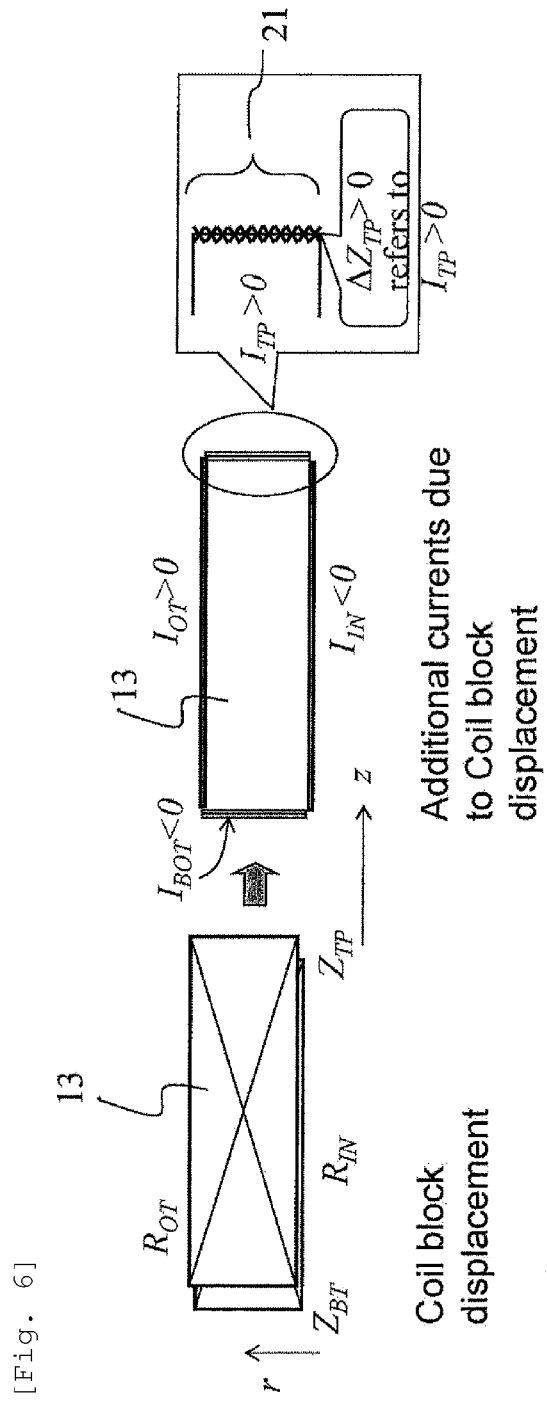
[Fig. 6]

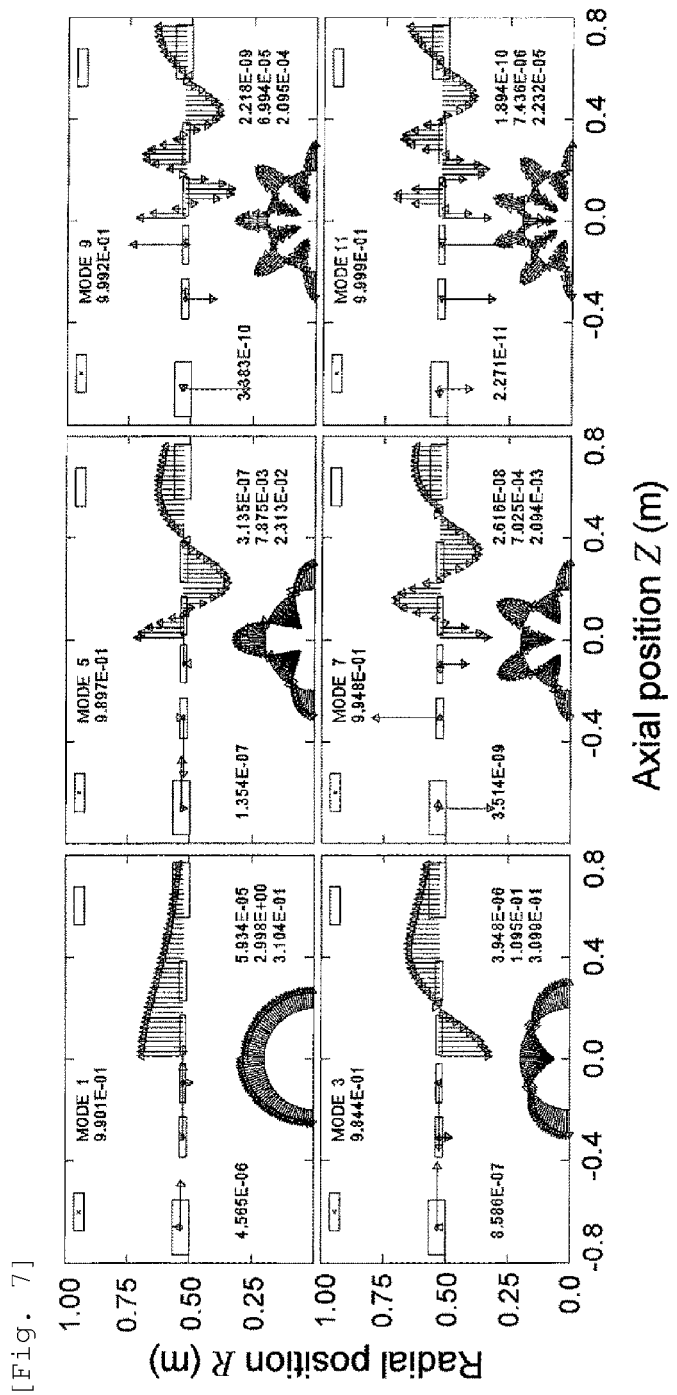
[Fig. 7]

[Fig. 8]
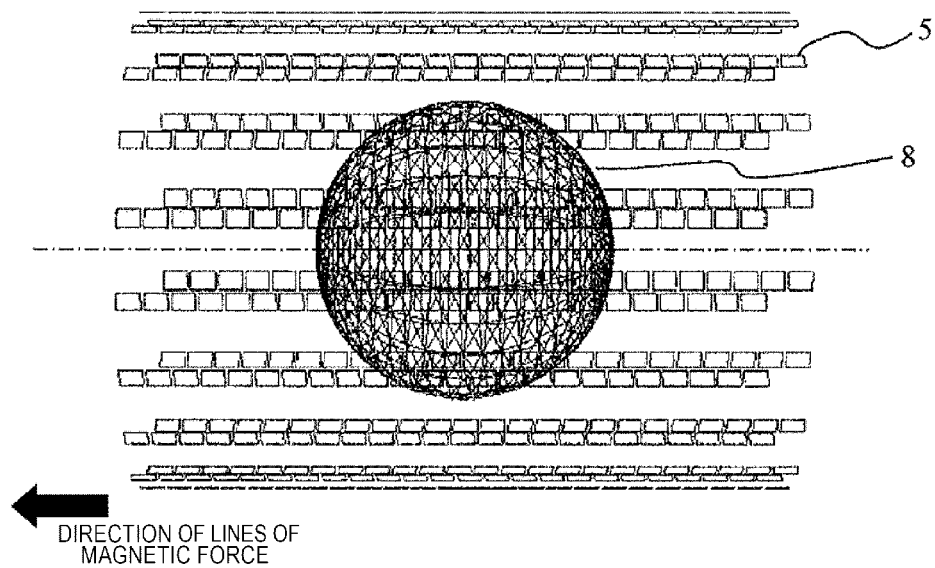
DIRECTION OF LINES OF
MAGNETIC FORCE

[Fig. 10]
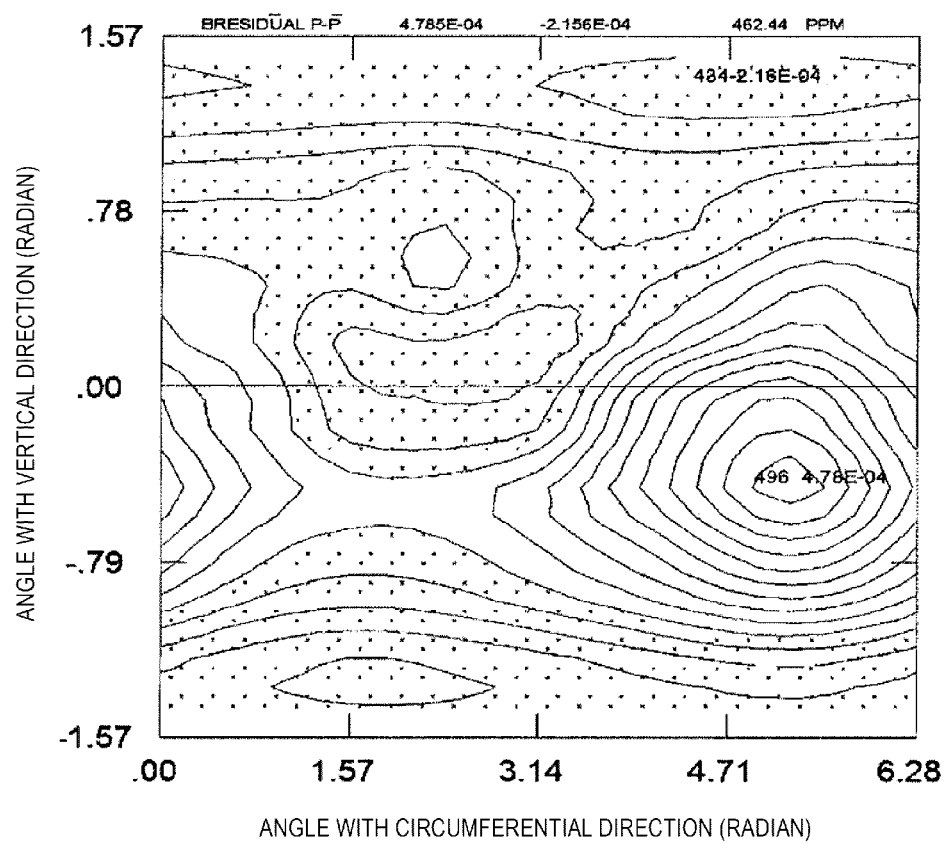

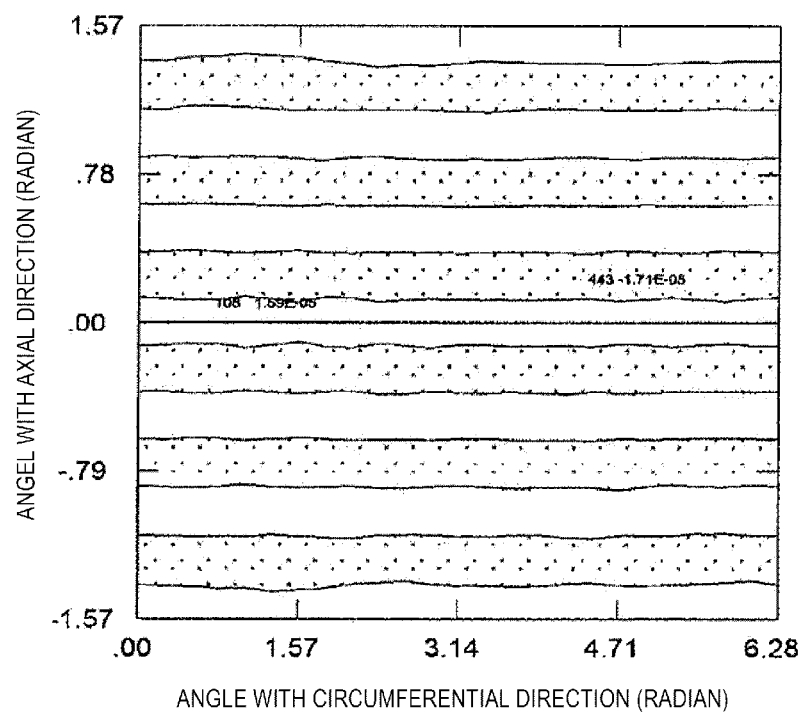
[Fig. 11]

[Fig. 12]
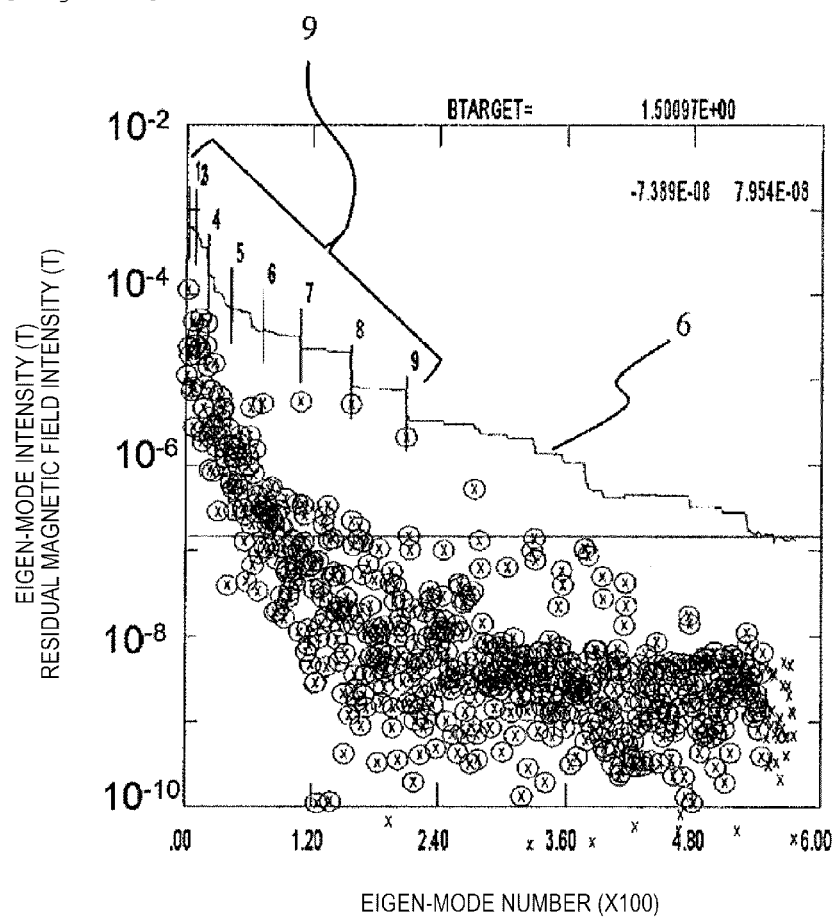

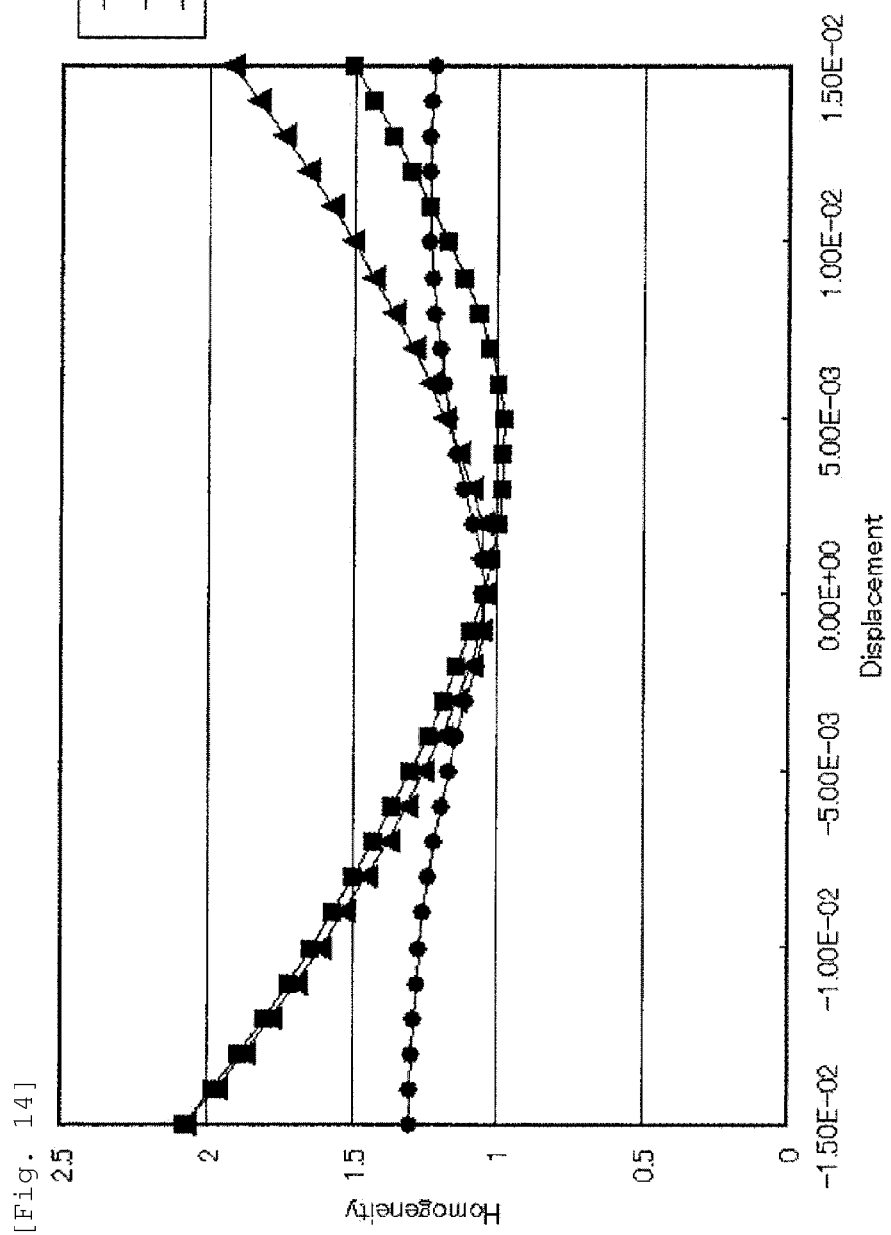
[Fig. 14]

[Fig. 15]
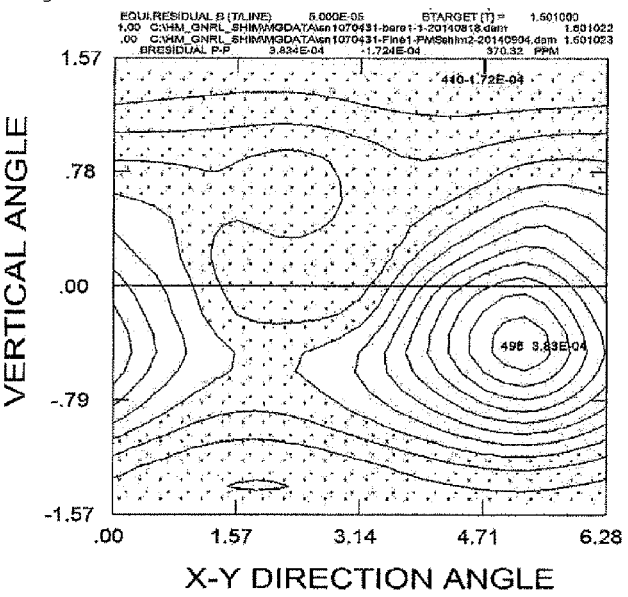

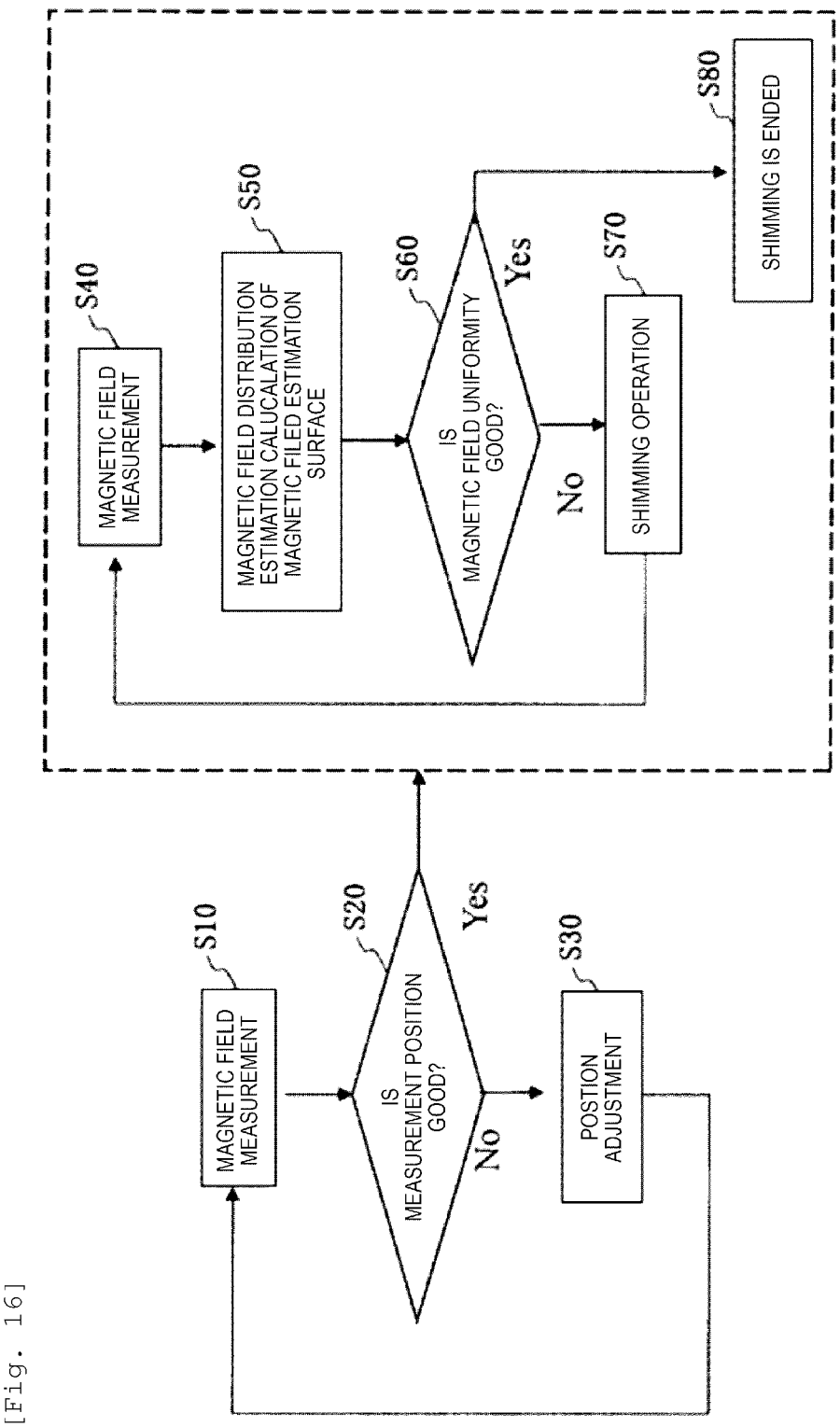

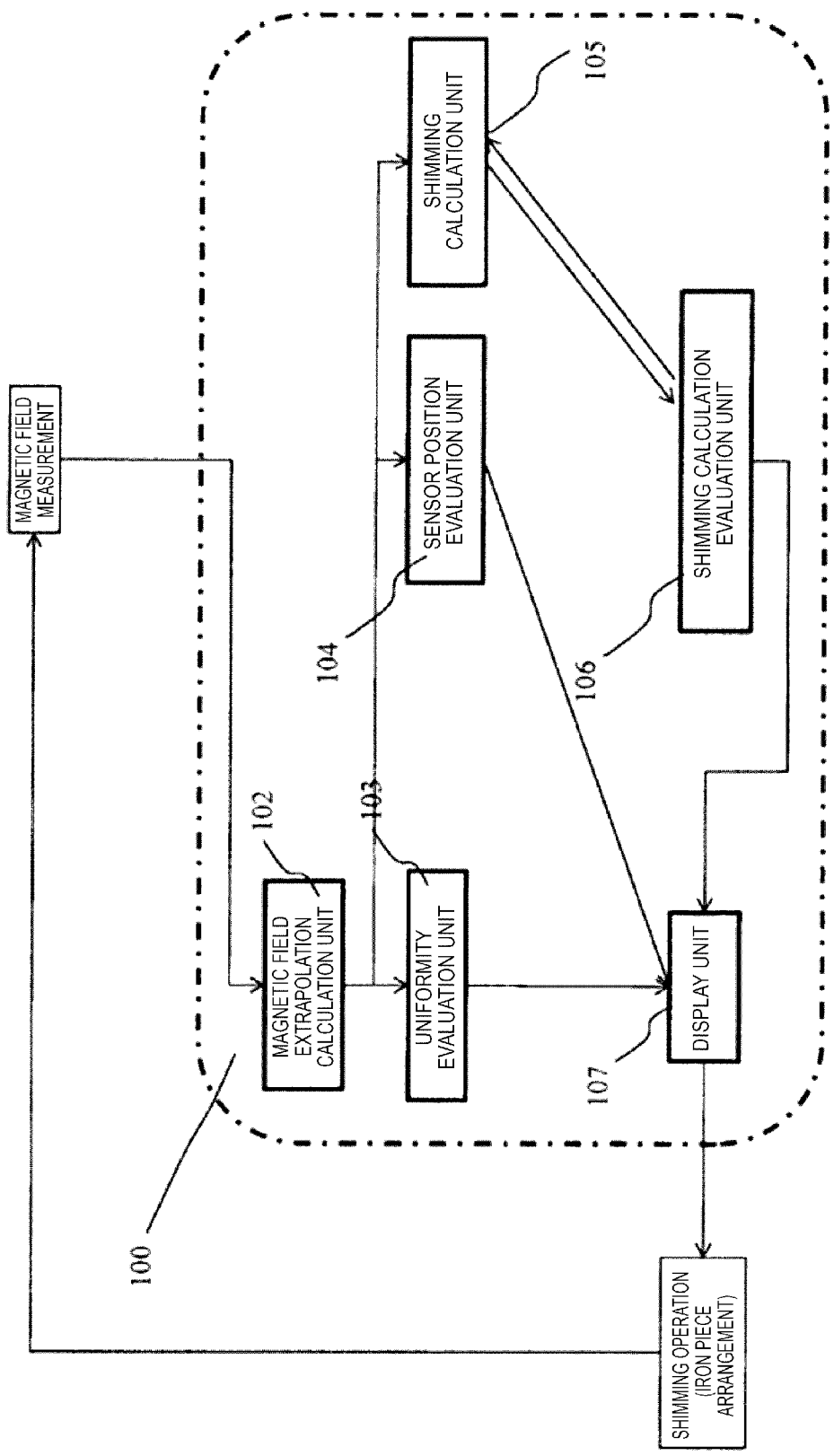
[Fig. 17]

SHIMMING SYSTEM AND SHIMMING METHOD INCLUDING A SENSOR UNIT HAVING A PLURALY OF MAGNETIC FIELD SENSORS

TECHNICAL FIELD

The present invention relates to a system and a magnetic-field-adjustment method of adjusting a magnetic field to a desired distribution of a magnetic field intensity in a magnet apparatus like a nuclear magnetic resonance imaging (MRI) apparatus used for medical diagnosis that generates a magnetic field by arranging a magnetic material such as a coil, iron, or the like.

BACKGROUND ART

In diagnosis using a nuclear magnetic resonance, a required accuracy in a magnetic field intensity of the magnet system is such that displacement of one millionth in a magnetic field intensity is considered to be a problem because a magnetic field intensity corresponds to a diagnosis place. There are three types of magnetic fields in MRI apparatuses. They are a static magnetic field, a gradient magnetic field, and high frequency magnetic field. That is:

(1) A magnetic field (static magnetic field) that is constant in time base and uniform spatially, and has an intensity of generally more than 0.1 to several tesla and a displacement range of about several ppm within a space for imagining (a space of a sphere or an ellipsoid with a diameter of 30 to 40 cm);

(2) A magnetic field (gradient magnetic field) varying with a time constant of about one second or shorter and inclined spatially; and (3) A magnetic field (high frequency magnetic field) caused by a high-frequency electromagnetic wave having a frequency (several MHz or higher) corresponding to the nuclear magnetic resonance.

The present invention is mainly related to the static magnetic field of (1), but in the magnetic resonance imaging apparatus, particularly in a region where tomographic imaging of a human body is performed, it is required that the distribution of the magnetic field intensity of the magnetic field is spatially constant in time base and uniformity with extremely high accuracy.

The high accuracy mentioned here is, for example, an imaging space Field of View (FOV) having a diameter of 40 cm, which requires an accuracy of a residual magnetic field of the order of one millionth such as ±1.5 ppm. In order to realize a magnetic field distribution requiring extremely high accuracy uniformity as described above, it is necessary to accurately adjust the magnetic field after production and excitation of a magnet.

Generally, an error magnetic field due to a production error is 1,000 times or greater a permissible error magnetic field required for a uniform magnetic field. Therefore, since the magnetic-field-adjustment (shimming) required at the time of installation after production is an operation to reduce the residual magnetic field (error magnetic field) from several 100 ppm to several ppm, a magnetic-field-adjustment apparatus and a method with extremely high accuracy are required.

As a related art, PTL 1 discloses a shimming method of performing arrangement calculation of a magnetic moment using singular value decomposition and implement based thereon. The method described herein is a method that uses censored singular value decomposition and a current potential, calculates the distribution of the magnetic moment or iron piece, and performs a shimming operation with a result thereof.

A mechanism (shimming mechanism) for implementing shimming by the method in the related art is shown in FIG. 2A. In the drawing, a magnetic field runs in a vertical direction on a paper surface, and an assumed magnetic resonance imaging apparatus is a vertical magnetic field type (open type) MRI apparatus.

Upper and lower circular faces are shim trays for arranging magnetic materials (shim pieces) such as iron pieces and magnet pieces, a shim piece to be arranged here flattens (shimming) the magnetic field distribution of a region of interest (VOI: Volume Of Interest, but here, a region to be subjected to magnetic field shimming including FOV) written with a spheroid at a central portion. That is, in PTL 1, a method of converting an obtained current distribution into a distribution of the magnetic moment and then converting into an amount of iron, a magnet or a small coil for shimming is described.

The outline of the calculation method in PTL 1 is as follows.

First, magnetism on the VOI is measured using a sensor (magnetic sensor) that measures magnetism, and a difference (error magnetic field) with a target error is obtained. Next, the distribution of the magnetic field that cancels the obtained error magnetic field is obtained from the shim piece on the shim tray by singular value decomposition on a response matrix to a large number (about several hundred points) of magnetic field evaluation points in the VOI region. Then, magnetic-field-adjustment (shimming) is performed using obtained eigen-modes (consisting of eigen-distribution functions of a shim piece distribution on the shim tray and the VOI magnetic field distribution, and singular values indicating the relationship therebetween). In the diagram presented in FIG. 2B, an error magnetic field component from a target magnetic field intensity of the VOI is decomposed into the intensity when represented by superposition of eigen-modes, and the singular values are sorted in order of magnitude and graphed. Among an eigen-mode group, it can be seen that an error magnetic field is generated in low-order (small singular value) eigen-modes. In PTL 1, large eigen-modes enclosed by a circle in FIG. 2B is selected and adjusted by magnetic-field-adjustment.

In addition, in NPL 1, in order to maintain the plasma within a predetermined space, a method of assuming a current plane consisting of a closed surface and determining a current distribution that reproduces the magnetic field on the plasma surface in a case where the plasma is confined in the inside surrounded by the closed surface is described. In NPL 1, a method of expressing a curved surface as a set of triangular elements and obtaining a current distribution that reproduces the magnetic field distribution given on the curved surface is described. The concept of grasping a curved surface as an aggregate of triangular elements is also common to PTL 1.

CITATION LIST

Patent Literature

PTL 1: Japanese Patent No. 4902787
PTL 2: Japanese Patent No. 4921935

Non Patent Literature

NPL 1: M. ABE, T. NAKAYAMA, S. OKAMURA, K. MATSUOKA, "A new technique to optimize coil winding path for the arbitrarily distributed magnetic field and application to a helical confinement system", Phys. Plasmas. Vol. 10, No. 4, (2003)$_{1022}$.

NPL 2: M. Abe, K. Shibata, "Consideration on Current and Coil Block Placements with Good Homogeneity for MRI Magnets using Truncated SVD", IEEE Trans. Magn., vol. 49, no. 6, pp. 2873-2880, June. 2013.

SUMMARY OF INVENTION

Technical Problem

However, in the shimming method of the related art, there was no study on a relationship between a measurement position of a magnetic field and an evaluation position of the magnetic field after adjustment. Specifically, in a case where the measurement position and the evaluation position are different, it is difficult to adjust the magnetic field with high accuracy by the technique of the related art. The present invention focuses on this problem and aims to provide a shimming method enabling highly accurate magnetic-field-adjustment even when the measurement position and the evaluation position are different.

Solution to Problem

In order to solve the above problem, various embodiments of the present invention are conceivable, as an example thereof, "a magnetic-field-adjustment assistance system including a magnetic field measurement device that has a sensor unit mutually fixed by using a mechanical mechanism and can perform magnetic field measurement of a large number of magnetic field measurement points and a magnetic-field-adjustment assistance unit that estimates a magnetic moment or current distribution that reproduces a magnetic field distribution obtained by the magnetic field measurement device on a predetermined closed surface, estimates a magnetic field distribution at an arbitrary point existing in the closed surface from the estimated magnetic moment or current distribution, and outputs a distribution of a shim magnetic material that generates an adjustment magnetic field for correcting the magnetic field distribution at the arbitrary point based on the estimated magnetic field distribution" can be mentioned.

Advantageous Effects of Invention

According to the present invention, it is possible to perform highly accurate magnetic-field-adjustment even in a case where a measurement position of a magnetic field and an evaluation position of an adjusted magnetic field are different.

BRIEF DESCRIPTION OF DRAWINGS

FIG. 1 is a diagram showing a representative example of a magnetic field estimation calculation system used in the present invention.

FIG. 2A shows a shimming calculation system in the shimming method of the related art, and FIG. 2B shows an eigen-mode intensity and eigen-modes selected for shimming.

FIG. 3 is an overall diagram of an MRI magnet and an MRI apparatus.

FIGS. 4A and 4B are a conceptual diagram of coil arrangement, showing a magnetic field intensity. FIG. 4A shows a radial contour map of coil arrangement and mag-
netic field intensity, the upper right diagram of FIG. 4B shows the case where the contour lines of the magnetic field intensity are six main coils, and the lower right diagram of FIG. 4B shows the case where the contour lines of the magnetic field intensity are seven main coils. A magnetic field contour line is indicated by ±1.5 ppm with respect to a target magnetic field. Also, the lines running horizontally in FIG. 4A are lines of magnetic force.

FIG. 5 shows a relationship between an eigen-mode and a current distribution of a magnetic field change occurring in coil deformation corresponding to an eigen-mode in the case of six main coils.

FIG. 6 is a diagram relating to a concept of a calculation method of a coil block arrangement, which shows a concept of considering a current on a side of a rectangular cross section of a coil, estimating a current value thereof, changing a side position, and optimizing a coil position and a cross-sectional shape at a stage of examining a continuous shape.

FIG. 7 shows eigen-modes of a magnetic field generated by positional fluctuation of a coaxially arranged coil block and deformation of a cross section.

FIG. 8 is a diagram showing a typical shimming calculation system of a horizontal magnetic field type MRI apparatus, which shows an arrangement of a shim tray (small square shape) and a magnetic field measurement surface (spherical surface).

Both

FIG. 10 shows a measurement magnetic field distribution.

FIG. 11 is a diagram of a magnetic field distribution at a measurement position when only high-order components are extracted.

FIG. 12 is a diagram showing a relationship between eigen-mode numbers uniform in a circumferential direction, eigen-mode intensities of a measurement magnetic field, and residual PP values of magnetic field estimation calculation.

FIG. 13A is a diagram where a seventh or more eigen-mode components uniform in the circumferential direction are reconsidered, and FIG. 13B is a diagram where eighth or more components are reconsidered.

FIG. 14 is a diagram showing the PP values of a residual magnetic field as a function of an amount of movement from an obtained magnetic field distribution in magnetic field calculation in a case where a magnetic field measurement center is moved in a high-order eigen-mode.

FIG. 15 is a diagram showing an example of a magnetic field distribution when a magnetic field distribution at a position of a radius of 20 cm is calculated by a magnetic field estimation calculation method of the present invention based on a magnetic field measured with a spherical surface having a radius of 25 cm.

FIG. 16 is a flowchart showing a magnetic field shimming process to which the present invention is applied.

FIG. 17 is a schematic diagram of a shimming system according to an embodiment of the present invention.

DESCRIPTION OF EMBODIMENTS

Explanation of Embodiment

Figure 9B:
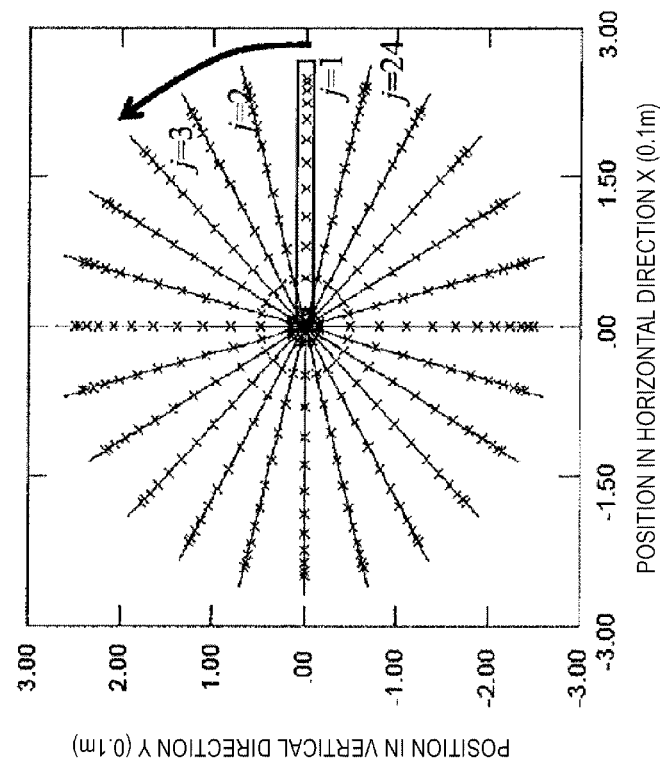
FIG. 9A and FIG. 9B are diagrams for explaining a magnetic sensor and a magnetic field measurement tool.

Before going into the description of the embodiment, a more detailed explanation will be given about PTL 1. In PTL 1, with a measurement position of a magnetic field as a magnetic field evaluation point, a magnetic moment such as an iron piece or the like is arranged so as to shim the magnetic field at the measurement position. When shimming is performed in this way, the uniformity of the magnetic field shows a good result in the vicinity of a magnetic field evaluation point position.

For example, as shown in FIG. 2A, the case of arranging the magnetic field evaluation point on a surface of a spherical surface or a spheroid (formed by rotating a half-moon or semi-ellipsoid about a central axis parallel to the lines of magnetic force) is considered. FIG. 2A shows a shimming calculation system in the shimming method of the related art, and FIG. 2B shows an eigen-mode intensity and eigen-modes selected for shimming. In this case, when the magnetic field evaluation points are arranged on a surface of a small sphere region and a center position of magnetic field measurement is arranged in a geometric apparatus central portion, the uniformity of the magnetic field may be good in a narrow region of the apparatus central portion, while the uniformity deteriorates somewhat in the outer region. In addition, conversely, when the magnetic field evaluation points are arranged on a large spherical surface, the magnetic field is uniform in the region near the wide spherical surface, but the uniformity is low around the small sphere region. For example, it is conceivable that the large spherical surface has a diameter of about 50 cm in MRI, and the small sphere has a diameter of about 20 to 45 cm.

It is desirable that a magnetic field component whose magnetic field changes for each fine region (an eigen-mode component having a large eigen-mode number as referred to in PTL 1) is measured by measuring the magnetic field at the large spherical surface and also the magnetic field evaluation surface at the time of shimming is enlarged. In this way, it can be said that it is necessary to determine the magnetic field evaluation position at the time of shimming separately from the magnetic field measurement position.

In actual shimming, the shimming operation is repeatedly performed even in shimming with respect to one magnet due to a physical quantity of the iron piece, an arrangement error, or the like, and a magnetic field evaluation surface position is sometimes changed during this shimming operation. In other words, in an early stage of the shimming operation (such as a first time), a larger spherical surface is defined as the magnetic field evaluation surface, and thereafter, a small spherical surface (or a spheroidal facing surface) is used as the magnetic field evaluation surface. In such a case, it is necessary to adopt the magnetic field evaluation surface separately from the magnetic field measurement surface.

Therefore, even in a case where a measurement position of the magnetic field and an evaluation position of the magnetic field are different, in order to improve the uniformity at the evaluation position of the magnetic field, it is conceivable to calculate and estimate the magnetic field at the evaluation position with high accuracy with respect to the magnetic field normally measured at several hundred points as one solution.

Hereinafter, a shimming method and a shimming system capable of performing shimming by estimating and calculating (extrapolation calculation) the magnetic field at a position different from the measurement position examined by the inventor of the present invention will be described.

First, PTL 1 describes a method of adjusting the magnetic field distribution (shimming) of the magnetic field distribution and obtaining a uniform magnetic field distribution in the vicinity of an FOV 4 before imaging after manufacturing the magnet. In this fine adjustment, singular value decomposition of the matrix is used as follows.

$$A = \Sigma u_i \lambda_i v_i^t \quad (1)$$

An approximately 100th eigen-mode from a relatively low-order eigen-mode (large singular value) obtained by the decomposition, is converted into an amount of the magnetic moment (equivalent to an amount of an iron piece or other magnetic material in passive shimming) necessary for the correction, and arranged on a shim tray 3. Here, $v_i$, $u_i$, and $\lambda_i$ are an i-th CP value distribution, an eigen-distribution of the magnetic field distribution, and a singular value (T/m) representing the conversion, respectively.

It is intuitively understood that $v_i$ is an amount of a magnetic material or magnetic moment to be arranged, $u_i$ is an eigen magnetic field distribution corresponding to $v_i$, and $\lambda_i$ represents how $u_i$ is output with respect to $v_i$, which is an amplification factor of $v_i$ with respect to $u_i$, so to speak. Therefore, the larger the $\lambda_i$, the stronger the intensity distribution of the magnetic field formed with respect to a small amount of magnetic material arrangement, while the smaller the $\lambda_i$, the lower the sensitivity of the intensity of the magnetic field generated with respect to the arrangement amount of the magnetic material. From this, it can be understood that the magnetic-field-adjustment which is efficient (achieving uniformity of the magnetic field intensity with the small amount of shim magnetic material arrangement) may be implemented focusing on the eigen-mode in which $\lambda_i$ is large. The eigen-mode number is a number assigned when numbers are assigned from a large eigen value.

Here, in PTL 1, the amount of the magnetic material to be arranged or the position of the magnetic material to be arranged during the shimming operation is obtained by singular value decomposition.

In contrast, in the present embodiment, an eigen-distribution of the magnetic field which reconstructs the measured measurement magnetic field distribution and a set (eigen-modes) of a current distribution corresponding to the eigen-distribution are obtained by singular value decomposition.

That is, the inventor paid attention to the fact that it is possible to reproduce the actually measured magnetic field distribution with high accuracy on the measurement position by adding a plurality of eigen-modes obtained by singular value decomposition. As a difference in calculation contents, PTL 1 shows that the magnetic field distribution to be reconstructed is the difference between a target magnetic field distribution and a measurement magnetic field distribution, in the case of the present embodiment, the magnetic field distribution to be reconstructed is the measurement magnetic field distribution itself.

The reconstruction calculation of the measurement magnetic field distribution is possible by executing the following calculation after magnetic field measurement. First, the arrangement of dipole moments that can accurately reproduce the measured magnetic field distribution is calculated. Thereafter, the calculation is implemented in the order that the magnetic field at the magnetic field measurement points are reconstructed from the magnetic field generated by each dipole moment.

In order to obtain the arrangement and the magnitude of the dipole moments, a virtually curved surface 8 including a region 1 (measurement surface 1) where the magnetic field measurement is performed is set. This virtually curved surface 8 can be recognized as an aggregate of triangular elements. Singular value decomposition can be performed by setting a model in which virtual current potentials are arranged at nodes between triangular elements (see FIG. 1). When the current potential is considered as a magnetic moment per unit area, the relationship therebetween is easy to understand.

As many eigen-modes as possible are obtained by this singular value decomposition. Because the reproducibility of the measurement magnetic field by one eigen-mode is limited, the more the eigen-modes are, the more accurate the reproducibility of the measurement magnetic field can be obtained. In order to obtain more eigen-modes, it is effective to increase the number of magnetic field measurement points or to construct the virtually curved surface 8 with finer triangular elements. The eigen-mode is recognized as a combination of the eigen-distribution of the magnetic field and the current distribution corresponding to the eigen-distribution. For this reason, an eigen-mode which is not obtained when a particle size is coarse is more likely to appear as the particle size of the measurement magnetic field and the arrangement granularity of the magnetic moments are finer, and the reproducibility of the measurement magnetic field can be increased.

Returning to the description of the reconstruction of the measurement magnetic field of the present embodiment, as many eigen-modes obtained by singular value decomposition as possible are added. As a result, the magnitude of the magnetic moments arranged at the nodes of the triangular elements described above is obtained. After arranging the obtained magnetic moment at each node, since the magnetic field intensity at an arbitrary point can be spatially calculated with high accuracy, it is possible to reproduce the measurement value of the magnetic field measurement surface 8.

Measurement of a magnetic sensor (magnetic field measurement instrument) is usually executed by using a magnetic sensor arranged on a spherical surface or an ellipsoid. Generally, in the shimming operation, the aim is to uniform the magnetic field distribution inside this measurement surface.

The center of the measurement position of the magnetic field distribution is originally a magnet center. However, even if dimensions are measured at a geometric center of a magnet instrument and the center of a measurement instrument is aligned with the center of the magnet instrument, the magnet center does not necessarily match the center of the magnetic field. In particular, in a case where the magnet equipment to be shimmed is a superconducting magnet, a superconducting coil exists in an extremely low temperature region. Therefore, it is extremely difficult to directly measure and grasp a positional relationship between the position of the coil and the magnetic field measurement surface.

In addition, in the MRI apparatus, since a gradient magnetic field coil and a high frequency antenna exist between the magnetic field measurement instrument and the magnet apparatus generating a uniform magnetic field, it is further difficult to grasp the positional relationship between the magnetic field center and the magnetic field measurement surface.

Shimming is possible even in a case where the center of the magnetic field and the center of the magnetic field measurement surface do not match. However, the uniformity that can be achieved with a limited amount of magnetic moment (an iron piece or the like) arrangement that can be realistically arranged decreases. The uniformity is a value obtained by dividing an amplitude (peak-to-peak) value of the error magnetic field in the FOV by an average magnetic field intensity and represented in ppm unit.

Here, the inventor has improved the method in which the position of the measurement surface has been determined with respect to an outer shape of the magnet or the gradient magnetic field, and paid attention to the possibility of improving the uniformity achieved by matching the measurement center and the magnetic field center.

In order to match the center position of the magnetic field measurement described above and the center position of the magnetic field formed by the magnet apparatus with each other, it is necessary to grasp the magnetic field distribution generated by the magnet apparatus. In the present example, a magnet design of the MRI apparatus is taken as an example, and the contents thereof will be described below.

In order to match the center of the magnetic field to be measured and the center of the measurement position, a basic concept in the following explanation is to grasp the magnetic field distribution reflecting the magnetomotive force arrangement (arrangement of the coil or the like) inside the magnet apparatus which is a magnetic field generation source and match the center of the magnetic field distribution and the center of the magnetic measurement surface. For that purpose, first, it is necessary to know the characteristics of the magnetic field distribution due to the magnetomotive force arrangement inside the magnet apparatus.

First, regarding the magnet apparatus in which a plurality of coils are arranged, a relationship between the arrangement of the coils and the magnetic field distribution formed by the arrangement will be described.

Regarding the magnetic field at the central portion of the magnet, NPL 2 and PTL 2 are referred. These documents show that the magnetic field distribution depends on the magnetomotive force arrangement of a coil block or an iron block in the magnet.

Further, as shown in NPL 2 and PTL 2, as an MRI magnet, a magnetic field is made up of a main coil that generates a strong magnetic field in an imaging region and a shield coil that reduces a leakage magnetic field to the surroundings, and a plurality of coil blocks are arranged, respectively. Regarding the magnetic field of the imaging region, the magnetic field generated by the shield coil is included, but the magnetic field of the imaging region is strongly influenced by the main coil arranged closer to the imaging region, and a discussion is also made relating to the main coil.

FIG. 3 is an overall diagram of an MRI magnet and an MRI apparatus. The magnet used for magnetic resonance imaging has an extremely uniform magnetic field intensity in the imaging region (FOV) 4, but the intensity is not completely uniform. As shown in these documents (NPL 2 and PTL 2), the magnetic field distribution in the imaging region of the magnetic field generated by the magnet is such that in the FOV 4, a portion where the magnetic field due to a member actually generating a magnetic field, such as a coil or an iron in the magnet is somewhat strong and, on the other hand, a portion where the magnetic field therebetween is somewhat weak alternately appear. In addition, when observing the strong magnetic field portion by the number of times of these intensities, the number of strong magnetic field portions corresponds to the number of convex portions of the coil block and the iron material. Furthermore, it is known that the number of strong magnetic field portions matches the number of axisymmetric eigen-modes symmetric with respect to a magnet axis obtained by singular value decomposition at the time of designing the magnet. That is, the intensity distribution of the magnetic field distribution observed in the vicinity of the FOV 4 reflects the magnetomotive force arrangement inside the magnet.

The magnetic field distribution in the vicinity of a magnet central portion will be described in detail. FIGS. 4A and 4B are a conceptual diagram of coil arrangement, showing a magnetic field intensity. FIG. 4A shows a radial contour map of the coil arrangement and the magnetic field intensity, the upper right diagram of FIG. 4B shows the case where the contour lines of the magnetic field intensity are six main coils, and the lower right diagram of FIG. 4B shows the case where the contour lines of the magnetic field intensity are seven main coils. In addition, FIGS. 4A and 4B show the magnetic field distribution in the FOV calculated and displayed according to the concept described in NPLs 1 and 2.

In FIG. 4B, the magnetic field distribution of the magnet center is represented by contour lines with a difference of ±1.5 ppm or more with respect to a central magnetic field. A hit point region represents a region where the magnetic field intensity is stronger than a target magnetic field (3 T in this diagram).

In FIG. 4A, the coil arrangement and the unevenness of the magnetic field intensity distribution are shown in a wider region than a focus image on the right side, schematically showing the magnetic field distribution in a design. Radially written contour lines represent the magnetic field intensity at ±1.5 ppm when six main coils are installed, as shown in FIG. 4B, for example. A line running horizontally as surrounding the main coil is a line of magnetic force. A horizontal axis is a geometric central axis of the magnet magnetic field (the direction of the axis is different in FIGS. 4A and 4B), which represents an axial position, and the coil arrangement and the magnetic field distribution are designed to be axially symmetrical with respect to this axis. A vertical axis represents a position in a radial direction.

A main coil block 12 is arranged close to the imaging region (around a radius of 50 cm in the diagram), and a shield coil block 11 is arranged far (around a radius of 1 m in the diagram). What is important in this diagram is that the region where the magnetic field is strengthened (hit point region) is connected to a main coil position. That is, the main coil creates a strong magnetic field region, and that region can reach the FOV, so the number of regions with a strong magnetic field and the number of the main coils match. When the singular value decomposition described above was applied to the relationship between such a magnetic field structure, and the main coil position and a cross-sectional shape making the structure, the following knowledge was obtained regarding the relationship between the coil arrangement and the eigen-distribution of the magnetic field.

FIG. 5 shows the relationship between the eigen-mode (lower part of each frame) and the current distribution (upper part of each frame) of the magnetic field change generated by the coil deformation corresponding to the eigen-mode in the case of six main coils. The difference between the right and left of each frame is that spatial constraint conditions of the current distribution are different when the eigen-mode is calculated.

The current distribution shown in the upper part of the right half of each frame shows the appearance of a large number of circular line currents arranged coaxially in a direction orthogonal to the direction of the horizontal axis. The direction of the arrow indicates the direction of the current, and the length of the arrow indicates the magnitude of the current. In each frame, the current distribution shown in the upper left part shows the change in the current distribution due to the coil deformation. The relationship between deformation of each coil block and the change in the current distribution is shown in FIG. 6. FIG. 6 is a diagram relating to a concept of a calculation method of the coil block arrangement, which shows a concept of considering a current on a side of a rectangular cross section of the coil, estimating a current value thereof, changing a side position, and optimizing a coil position and a cross-sectional shape at a stage of examining a continuous shape. In FIG. 6, for example, in a case where the coil block 13 is deformed so as to swell to the right side, when this change is considered from a viewpoint of the current distribution, it is possible to capture the deformation of the coil block as a phenomenon in which a current distribution of a new coil current appears at a position that did not exist before the deformation. The upper part of the left half of each frame in FIG. 5 shows how the current distribution with respect to the eigen-distribution is captured as a change in current distribution due to the coil deformation.

The frame at the bottom right of FIG. 5 is not an eigen-mode (MODE HIGH), but a distribution vector of the magnetic field and the current is assumed to be a vector having all is as elements, and the distribution obtained by subtracting all the components of the eigen-modes up to the thirteenth is normalized. In other words, the frame at the bottom right of FIG. 5 shows a distribution that cannot be expressed by the obtained eigen-mode. In this frame, the numerical values are the magnetic field intensity (root mean square rms) per unit current vector obtained by the coil deformation and the coil current model.

In addition, the numerical values in the upper part of each frame in FIG. 5 shows the number of each eigen-mode and the inner product of the distribution of the left and right magnetic fields, and the inner product, 1.0 means exactly the same distribution. Even in the distribution model of a coil current having a high degree of spatial arrangement freedom and in the case of adopting the current distribution model provided with the conditions of actual coil shape and arrangement, the fact that the inner product of the eigen-distribution is close to 1 in all eigen-modes, indicates that almost the same eigen-distribution can be obtained. That is, it is understood that the eigen-mode does not depend on the shape of a current source, but depends on the shape of a cylindrical solenoid in which the current source is arranged, and the following discussion can be applied to magnets in which coaxial coil arrangement is performed such as MRI in a versatile manner.

In addition, singular values are shown for the two current models at the lower part of each frame in FIG. 5. In addition, among the numerical values shown on the right side of the lower part of each frame, below the singular value (first stage), the magnetic field intensity (root mean square rms T) that each eigen-mode takes to generate a uniform magnetic field (here, 3 T is taken as an example) is shown. Since the magnetic field distribution for the two current distribution models is illustrated in each frame, the magnetic field intensity taken for generating a uniform magnetic field is represented for each magnetic field distribution.

In addition, an amount of a current that generates a unit magnetic field intensity (rms value) can be understood as the reciprocal of this singular value (here, the unit is the magnetic field intensity per unit current T/A) $\lambda_i$. That is, the error magnetic field for a low-order (large singular value) eigen-mode can be easily corrected by the method of PTL 1, when the number of the eigen-mode having a number greater than 100 is increased in PTL 1, shimming cannot be done sufficiently with limited a shimming capacity (current or magnetic material).

In particular, in the case of capturing the magnetic field distribution shown in FIG. 4B as the magnetic field distribution of the eigen-mode depending on the coil arrangement itself as shown in FIG. 4A, it is difficult to shim this eigen-mode itself. In the upper side of FIG. 4B, there are six high magnetic field portions, and the main coil has six magnets. In addition, in the lower side of FIG. 4B, there are seven high magnetic field regions, which is the magnetic field by the magnet in the case of seven main coils. In order to correct the magnetic field for the eigen-modes dependent on such coil arrangement itself, a large current or iron material equivalent to one coil is required, and shimming is not actually possible. That is, it is necessary to keep such high-order eigen-modes as small as possible at the time of designing, and the magnetic field of this high-order eigen-modes will remain after shimming irrespective of the shimming method.

Here, the order of eigen-modes is numbered in ascending order of singular values. A high-order mode refers to an eigen-mode having a magnetic field equal to or higher than the number of coils, when FIG. 5 is adopted as an example, since the number Nm of the main coil blocks 12 is 6 (Nm=6), the high-order mode does not include an eleventh number of the mode number (2 Nm−1) by which six high magnetic field portions can be checked with the magnetic field distribution and refers to an eigen-mode having an eigen value smaller than the eleventh number. Therefore, an eigen-mode including a (2 Nm+1)th eigen-mode and an even smaller eigen value is a high-order. In FIGS. 4A and 4B, a discussion is made relating to the number of coils, but there is not only the coil block 13, but also an MRI magnet that uses an iron material and a permanent magnet. In this case, it is reasonable to understand that Nm is not the number of coil blocks, but the number of regions where the magnetic field is strong. The numbers of the eigen-modes in FIGS. 4A and 4B shows only the upper half of the modes that appear vertically symmetrically when a solenoid coil is cut with a plane that is horizontal in a certain axial direction.

Similarly, the eigen-modes with respect to the movement of the coil position are compared with the eigen-modes by the coil current and are shown in FIG. 7. Any diagram of FIG. 7 is a diagram showing eigen-modes of a magnetic field generated by positional fluctuation of a coaxially arranged coil block and deformation of a cross section. The concept relating the eigen-modes with respect to the movement of the coil position is basically the same as the eigen-modes for coil deformation. The numerical values written in each frame have the same contents as in FIG. 5. In this diagram, only the movement of the coil block position is performed, and deformation of the cross-sectional shape is not taken into consideration, so the degree of freedom of the coil movement is smaller than that in the case of FIG. 5. Therefore, the number of axially symmetric eigen-modes is limited to six. Accordingly, the high-order eigen-modes cannot be changed/adjusted. However, similarly to the case of FIG. 6, the eigen-modes of the coil current and the eigen-mode distribution of the position movement of the coil block 13 are almost the same.

To summarize the discussion so far, regarding the magnetic field generated by the magnet apparatus, the magnetic field distribution formed from high-order components of the eigen-modes reflects the number and arrangement of the main coil blocks 12 in the magnet apparatus. Even if there is deformation or movement of the main coil blocks 12, it can be said that the eigen magnetic field distribution before deformation and the eigen magnetic field distribution after deformation are similar eigen-distributions. Therefore, even if the coil block 13 has deformation or movement in the cross section thereof, it is reasonable that the eigen magnetic field distribution having the same number of magnetic field convex regions as the number Nm of the main coil blocks 12, that is, the eigen-modes of (2 Nm+1)th or higher (small singular value) is considered as a high-order mode.

In addition, in all cases, the singular values show that the magnetic field per unit current decreases by one digit each time the convex portion (high field region) of the magnetic field distribution increases by one. That is, in the high-order mode, a current of 105 times or more than a fundamental mode (first) is required, and conversely, even if an error component corresponding to 100 kA exists in the high-order mode, only a magnetic field of about 1 p tesla is generated. Therefore, the error magnetic field having such high-order eigen-modes cannot be corrected, and conversely, even when there is an assembly error in the magnet, since the eigen-modes of the high-order components are small, it can be said that the high-order eigen-mode components of the actual machine magnet is the original magnetic field distribution of the magnet in the design.

In the shimming method of PTL 1, the current potential distribution on the arrangement surface is obtained by singular value decomposition on a response matrix from the magnetic moment on the arrangement surface (shim tray) to the magnetic field distribution, the arrangement of magnetic moments is calculated by using the low-order part of the eigen-modes, and in an actual operation, magnetic moments such as iron pieces are arranged according to a calculation result.

In the high-order eigen-modes (small singular value), required iron pieces or a current value is a subject. The intensity of the eigen magnetic field distribution with respect to the unit current is very small, so shimming is unnecessary. Since the eigen-mode shown in FIGS. 2A and 2B also includes the eigen-mode distributed in the circumferential direction, many eigen-modes exist. However, an actual number of eigen-modes for shimming is about 100 in the diagram, which is up to about (2 Nm−1)th eigen-mode component of the axisymmetric components at the top. That is, in Nm=6 and Nm=7 in FIG. 4B, the eigen-mode number of the axisymmetric components is limited to about 11, 13, or lower, respectively. Conversely, up to an Nm-th in the axisymmetric eigen-mode number, at the time of magnet design, the eigen-mode intensity is adjusted to generate a uniform magnetic field, and the error eigen-mode intensity due to the error magnetic field is small, so it can be said that shimming is easy.

As described above, it can be said that there is no change in the magnetic field distribution of high-order components even before and after shimming. In addition, the high-order component magnetic field reflects the arrangement of the main coil block 12 inside the magnet. Furthermore, the magnetic field is designed so that such high-order eigen-mode components remain even at the time of magnet design.

In the shimming of PTL 1, shimming can be performed on a measurement magnetic field by calculations in a computer without actual shimming. Shimming of a real machine is executed with conditions (such as a target magnetic field or selection of an eigen-mode to be considered at the time of shimming) where good shimming results can be expected by the calculations performed in the computer.

In the magnetic field measurement, since the magnetic field is measured every 10 to 30 degrees in the circumferential direction, and the distribution of the obtained magnetic field intensity is used as an input variable for shimming calculations, by developing this magnetic field distribution to eigen-distributions and selecting an eigen-distribution of a uniform component in the circumferential direction among the eigen-distributions, an eigen-mode component can also be detected. In addition, when comparing the eigen-mode components uniform in the circumferential direction and the magnetic field distribution of FIGS. 4A and 4B that the magnet has in the design with the number of regions where the magnetic field is strong (the region where the magnetic field intensity is convex), it is possible to detect the eigen-mode which generates the magnetic field distribution of FIGS. 4A and 4B by the eigen-mode number at the time of shimming. Then, when an eigen-mode which is smaller than the singular value of the eigen-mode where the number of regions where the magnetic field is strong and the number of main coils match is selected and the magnetic field of the eigen-mode component is added, it is possible to extract the magnetic field of the high-order eigen-mode components remaining in the magnetic field design from the measurement magnetic field.

The high-order eigen-mode magnetic field extracted in this manner is a magnetic field reflecting the arrangement of the coil blocks inside the magnet. The center of the magnetic field can be estimated by using this high-order eigen-mode magnetic field. That is, by estimating and calculating the residual magnetic field by the high-order eigen-modes with the magnetic field reconstruction using singular value decomposition, and moving the center of the magnetic field evaluation point to the position expected to be the smallest, it is possible to perform shimming.

As described above, by using the magnetic field calculation method invented by the present inventor, the magnetic field intensity can be calculated at an arbitrary position different from the measurement position on the magnetic field measurement surface. In addition, it is possible to grasp the magnetic field distribution for each eigen-mode. By using this principle, since the magnetic field at an arbitrary point can be calculated, it is possible to select a magnetic field evaluation point and a magnetic field reinforcement surface so that the magnetic field distribution of a targeted position/region is more uniform. In addition, information on the magnetomotive force arrangement in the magnet can be obtained from the high-order components difficult to shim with less influence of the error magnetic field, and from the information, it is possible to adjust the magnetic sensor position at the time of magnetic field measurement and the magnetic field evaluation surface position at the time of shimming.

As a result, it is possible to obtain a better uniformity suitable for imaging in the MRI apparatus.

Example 1

Hereinafter, the conceptual contents of the present invention explained so far will be described more in detail.

As a first example, the position adjustment of the magnetic field measurement position at the time of shimming of a horizontal magnetic field type MRI apparatus will be described. The measurement position referred to here is not an individual magnetic sensor position but a position of a tool for supporting the magnetic sensor, or is a center position of the magnetic field measurement surface 8 which is the spherical surface or spheroid. In addition, FIG. 17 shows an outline of a shimming system 100 capable of adjusting the magnetic field measurement position described in the present example.

As shown in FIG. 17, the shimming system of the present example includes a magnetic field extrapolation calculation unit 102, a uniformity evaluation unit 103, a sensor position evaluation unit 104, a shimming calculation unit 105, a shimming calculation evaluation unit 105, and a display unit 107 as a main configuration. In addition, the direction of the arrow in the diagram shows the flow of input and output of information on each functional block.

First, as a premise, regarding a static magnetic field of the horizontal magnetic field type MRI apparatus, the concept relating to the present invention will be explained. FIG. 1 is a diagram showing a representative example of a magnetic field estimation calculation system used in the example of the present embodiment, in which there is the magnetic field measurement surface 8 on the inside and on the outside, there is a virtual current plane 1 assuming current distribution on the calculation. The virtual current plane 1 is a closed surface. In addition, even in a case where there is an opening portion, the size of the opening portion is a curved surface whose solid angle from the center of the device is about 1/10 or less of $4\pi$ and surrounds the magnetic field measurement surface 8 as a whole.

FIG. 8 is a diagram showing a typical shimming calculation system of a horizontal magnetic field type MRI apparatus, which shows an arrangement of a shim tray (small square shape) and a magnetic field measurement surface (spherical surface). In addition, both FIG. 9A and FIG. 9B are diagrams for explaining a magnetic sensor and a magnetic field measurement tool.

Figure 9A:
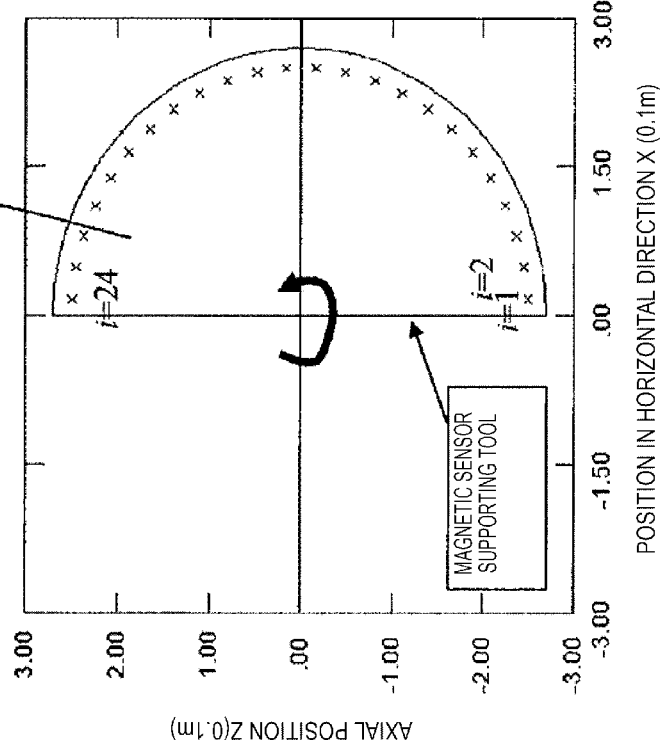

In actual shimming, a shim pocket 5 group arranged in a rod-like shim tray and arranged as shown in FIG. 8 and the magnetic field measurement tool rotationally symmetric about a rotation axis parallel to a horizontal magnetic field as shown in FIG. 9A are used. The shim pocket 5 is usually arranged inside a gradient magnetic field coil 24 (see FIG. 3) having a cylindrical shape, the shim pocket 5 group is also arranged in a cylindrical shape as a whole, and the shim pocket 5 (thus the magnetic material for shimming) is arranged to surround the magnetic field measurement surface 8.

A magnetic sensor support plate 20 in FIG. 9A is a part of a supporting tool (not shown) whose central axis is a rotation axis, but a magnetic sensor (indicated by x in the diagram) is fixed to the plate. 24 pieces (i=1 to 24) are arranged in the diagram, in FIG. 9B, the magnetic field measurement is performed on the magnetic field measurement surface (j=1 to 24) of 24 surfaces in the circumferential direction. As a result, magnetic field measurement can be performed at 576 points on the magnetic field measurement surface 8 (the spherical surface in this case).

These magnetic field measurement points are arranged on the spherical surface, and by changing the fixed position of the tool, it is possible to move all the magnetic field measurement positions at the same time in the same magnitude and direction. The amount and direction of this movement are described below as the movement of the center of the magnetic field measurement position. In addition, the position regarded as the center position of the magnetic field measurement is a position which is an origin in FIG. 9A, and a center position in the axial direction on the rotation axis of the semicircular shape of the magnetic sensor support plate 20. The position is also a geometric mean value of the magnetic field measurement position.

A magnetic field measurement value $B_i$ is a magnetic field intensity value measured on the magnetic field measurement surface 8. In a magnet which a general MRI apparatus has to provide a uniform magnetic field, the magnetic field is substantially in the axial direction (Z direction). In addition, when the virtual current plane 1 is represented by a set of triangular elements and a current potential (CP) Tj is placed at a contact point j, the distribution of CP values on the virtual current plane 1 is represented by a vector, T. In addition, a magnetic field Bj of the measurement points on the magnetic field measurement surface 8 is also represented as vector B. Here, the current potential is discussed in PTL 1 and NPL 1, but although a normal current potential has a magnetic moment in a direction perpendicular to the surface, in this case, the current potential is virtually assumed to be a component parallel to the axis (Z) direction.

The relationship between the CP value and the magnetic field is in a linear equation, the equation is as follows.

$$B = AT \quad (2)$$

A is a response matrix from the current potential to the magnetic field. A is approximately solved by using regularization by a censored singular value decomposition method.

With singular value decomposition, the response matrix A can be decomposed as follows.

$$A = \Sigma u_i \lambda_i v_i^t \quad (3)$$

Here, $v_i$, $u_i$, and $\lambda_i$ are an i-th CP value distribution, an eigen-distribution of the magnetic field distribution, and a singular value (T/m) representing the conversion, respectively. Using this, the CP value distribution is multiplied by the following equation so that a target magnetic field $B^{TG}$ is reproduced, the equation is as follows.

$$T = \Sigma n_p^{1/2} P_i^{TG} v_i / \lambda_i [A, m^3, \text{ or } Am^t] \quad (4)$$

Here, $n_p$ is the number of magnetic field measurement points, $P_i^{TG}$ is the following equation by using the inner product of the magnetic field distribution and the eigen-distribution of the magnetic field, and $P_i^{TG}$ is an eigen-mode intensity required to reconstruct $B^{TG}$, the equation thereof is as follows.

$$P_i^{TG} = u_i^t B^{TG} / n_p^{1/2} [T] \quad (5)$$

In Equation (5), addition can be done with respect to the same number of eigen-modes as the rank number of the matrix A. However, it is not necessary to add up to that limit. In PTL 1, since the magnetic field is adjusted, the obtained magnetic field uniformity is executed up to the order sufficient for a magnet specification, and a high-order higher than that is ignored. Here, $B^{TG}$ is a magnetic field generated by iron pieces and the like by shimming, and the difference between the final target magnetic field (for example, a 3 T uniform magnetic field $B^{3T}$) and a measurement magnetic field $B^{Ms}$, the equation thereof is as follows.

$$B^{TG} = B^{3T} - B^{Ms} \quad (6)$$

In the present example, attention is paid to the magnetic field of the high-order eigen-mode components which have information on the magnetomotive force arrangement of the magnet and is hardly affected by the error magnetic field. Specifically, when a number has an order corresponding to the number of coils and the number of the eigen-modes uniform in the circumferential direction is assumed to be a M-th, eigen-modes having a small singular value less than a singular value $\lambda_M$ are considered as a high order, and addition relating to such eigen-modes is executed by Equation (4). This calculation is addition relating to the high-order modes unlike the case where shimming for adjusting the magnetic field is performed only in the low order in the related art.

The magnetic field distribution can calculate the magnetic field for an arbitrary point within the region surrounded by the virtual current plane 1 by using the current potential distribution obtained by Equation (4). In addition, a magnetic field $B^{REC}$ that reproduces the difference $B^{TG}$ between the magnetic field at the measurement point and the measurement magnetic field is as follows.

$$B^{REC} = \Sigma n_p^{1/2} P_i^{TG} u_i \quad (7)$$

This magnetic field is used. It is a key point of the present example to execute reconstruction of this magnetic field distribution or current potential (Equations (7) and (4)) only with the high-order eigen-mode components.

For Nm=6 magnets as shown in the upper portion of FIG. 4B, on the magnetic field measurement surface 8 shown in FIG. 8, FIG. 10 shows a contour line distribution of the magnetic field measured using the magnetic sensor shown in FIG. 9A. In FIG. 10, the vertical axis is an angle with the central axis in the horizontal direction in FIG. 8, and the horizontal axis is an angle around the central axis indicated by a one-dot chain line. An angle 0 is an X axis, and is the direction perpendicular to the page surface in FIG. 8. An Y axis is in the direction of 90 degrees. The hit point region is a magnetic field higher than the target magnetic field (1.5 T in this case) ($B^{TG}_i$ is a negative area, $B^{TG}_i$ is the target magnetic field intensity of an i-th measurement point). The hit point region is measured on the spherical surface having a diameter of 50 cm (hereinafter, referred to as 50 cm DSV, DSV is Diameter Spherical Volume).

Next, an example of applying the magnetic field estimation calculation in the system of FIG. 1 to this measurement magnetic field will be discussed. This magnetic field estimation calculation is calculation contents in the magnetic field extrapolation calculation unit 102 (see FIG. 17) described above. The high-order eigen-modes obtained by singular value decomposition of the measurement magnetic field, are close to the magnetic field that the magnet originally has, as already described. FIG. 11 shows the magnetic field distribution according to the eigen-distribution obtained by adding the high-order eigen-modes as much as possible. In this diagram, the vertical axis Z indicates a position in the axial direction and the horizontal axis X indicates the horizontal direction, which shows the magnetic field distribution in an X-Z plane. The magnetic field intensity is indicated by contour lines, and the portion with higher magnetic field than the target magnetic field (high-order eigen-mode components necessary for a 1.5 T uniform magnetic field) is set as the hit point region, a non-hit point region is a region where the measurement magnetic field is slightly high. The magnetic field distribution formed by the high-order eigen-modes is obtained from Equation (7). In this example, the magnetic field distribution is reconstructed by superimposing the eigen-modes having a singular value smaller than that of the high-order eigen-modes where seven strong magnetic fields exist, that is, eigen-modes having 7 or more magnetic fields with a strong intensity in the eigen-distribution.

This magnetic field distribution matches the magnetic field intensity distribution at the time of designing the magnet in FIG. 4A and becomes a strip magnetic field distribution in the circumferential direction corresponding to six main coils in the circumferential direction, indicating that high-order components can be extracted.

A specific example of a method for extracting high-order modes from the measurement magnetic field is shown. Here, the eigen-mode components are a magnetic field distribution reproduced by obtaining the eigen-mode intensity $P_i^{TG}$ by developing the eigen-mode by using Equation (5), and using an eigen-mode $u_i^t$ of the magnetic field, for the magnetic field of Equation (6).

When this magnetic field is represented by a graph numbered in order of eigen-mode intensity and a singular value, the distribution is as shown in FIG. 12. FIG. 12 is a diagram showing a relationship between eigen-mode numbers uniform in the circumferential direction, eigen-mode intensities of a measurement magnetic field, and residual PP values of magnetic field estimation calculation. The intensities of many eigen-modes (absolute value of Equation (5)) are plotted on a logarithmic axis, but there are slightly strong eigen-modes at the position indicated by a line segment parallel to the vertical axis. The slightly strong eigen-modes are eigen-modes uniform in the (circumferential) direction around the axis and are defined as a basic eigen-mode group 9.

Among these eigen-modes, in the basic eigen-modes up to Nm, which are uniform in the circumferential direction and axially symmetric, the residual magnetic field of the difference between the magnetic field $B^{ES}$ by the coil arrangement at the time of designing the magnet and the uniform magnetic field $B^{3T}$ is designed to be close to zero, the equation thereof is as follows.

$$B^{RE} = B^{3T} - B^{DS} \quad (8)$$

By generally using Equation (5), an eigen-mode intensity $P_i$ is as follows.

$$P_i = u_i' B^{RE} / n_p^{1/2} [T] \quad (9)$$

But the eigen-mode intensity of the residual magnetic field is $P_i^{RE} = u_i' B^{RE} / n_p^{1/2}$.

The eigen-mode intensity at the time of designing can be brought closer to zero for the Nm-th or lower basic eigen-modes uniform in the circumferential direction by shimming. However, for the (Nm+1)th or higher eigen-modes uniform in the circumferential direction, it is difficult to design such that the eigen-mode intensity becomes zero. In these high-order eigen-modes, the magnet has a finite length, and this is because magnetic field components are generated due to discrete arrangement of coil groups having a rectangular cross section in the magnet, which is a residual magnetic field inevitably occurring in a so-called realistic magnet in the design. Actually, in FIG. 12 as well, Nm=6, and a sixth eigen component uniform in the circumferential direction has the same magnitude compared to the other eigen-modes. The intensity is stronger than the low-order eigen-modes, because the error magnetic field appears in the low order. In addition, the low-order eigen-modes can be corrected by the shimming operation according to the method disclosed in PTL 1. The contents calculation of the shimming operation is executed by the shimming calculation unit 105 or the shimming calculation evaluation unit 106 shown in FIG. 17.

Generally, after the magnet is produced, installed, and excited, the measurement magnetic field becomes a magnetic field including an error magnetic field derived from assembling error or the like with respect to the magnetic field at the time of designing. However, these error magnetic fields are magnetic fields belonging to a relatively low-order eigen-mode, and a high-order component is hardly included in the error magnetic fields. Here, the high-order components are an eigen-mode group that also includes a non-axisymmetric component having an eigen value of the singular value $\lambda_M$ smaller than the Nm-th eigen-mode of the eigen-modes which are uniform in the circumferential direction and axisymmetric. Conversely, the eigen-modes having a singular value larger than $\lambda_M$ will be referred to as a low-order eigen-mode. When the current potential is reconstructed according to the high-order eigen-modes from the eigen-modes of the high-order components by Equation (4) and the magnetic field distribution is calculated by Equation (1), a magnetic field of the high-order components is extracted from the measurement magnetic field. Extraction of the magnetic field (eigen-distribution) of these high-order components is executed by the sensor position evaluation unit 104.

Discussion of the high-order components so far is about discarding the low-order eigen-mode, but conditions for adding eigen-modes on the highest-order side will be discussed as well.

There are as many eigen-mode numbers as the number of ranks of the response matrix A, and an upper limit of addition in Equations (3) and (4) can be up to the highest-order eigen-mode of a rank number. Since the number of nodes in the virtual current plane 1 is larger than the magnetic field measurement points, practically, eigen-modes exist to the extent of the number of nodes of the virtual current plane 1. However, due to the capability of the computer (the resolution of the magnitude of numerical values), actually, it is not possible to grasp eigen-modes with an extremely small eigen value. When trying to compute forcefully, computational errors may be included, which may adversely affect subsequent discussions. Therefore, the upper limit of the eigen-mode number is selected by approximation accuracy of the magnetic field. There are the following three ways of concept and any one may be adopted.

(1) Evaluate approximation accuracy for the measurement magnetic field and select an upper limit (Mu) so as to obtain sufficient accuracy.

(2) Evaluate the magnitude of each eigen-mode and discard small contributions.

(3) Combine both.

When target accuracy is assumed to be Ere (unit is T, tesla), the accuracy corresponds to the sufficient accuracy of (1) and depends on the performance of an apparatus, but in MRI, it is necessary to make an error of the order of the target magnetic field $\pm 10^{-6}$, so that the error is less than $\pm 0.15$ μT in 1.5 T. Here, Ere=0.1 μT is assumed. Therefore, the peak-to-peak value of the error is 0.2 μT. The Mu is determined to satisfy this condition.

In method (2), $P_i^{TG}$ whose value is Pmn=0.05 μT or less is discarded. Here, the reason why $P_i^{TG}$ is set smaller than the accuracy of (1) is because the accuracy obtained actually is obtained by superimposing many eigen-modes, so the contribution of each high-order eigen-mode discarded is kept small.

Method (3) is a combination of both methods. The method is adjusted so that sufficient accuracy can be obtained with two variables Mu and Pnm. There are trials and errors, but actually, Pnm is set sufficiently small (for example, on the order of $10^{-10}$ T or less) and is set to an extent that does not affect the uniformity, and a relationship between Mu and the reached uniformity is displayed in a graph. This is the polygonal line shown in FIG. 12 (the magnetic field PP value 6 indicated by a rough eigen-mode upper limit function). Mu is selected so that the vertical axis of this polygonal line is equal to or less than Eer.

Selection of an eigen-mode is described in FIG. 12. In the diagram, the broken line shows the difference between a magnetic field estimation calculation value obtained by adding each eigen-mode and an original measurement magnetic field (FIG. 10), with a maximum minimum peak-to-peak (PP) value 6 in the measurement magnetic field of several hundred points. About 570 eigen-modes can be calculated in this diagram. When about 550 error magnetic fields close to the eigen-modes are selected, the error magnetic field PP value is below 0.2 micro T (μT). That is, the error is within ±0.1 micro T.

In FIG. 12, the numerical values in the upper right corner of the frame are the maximum and minimum values of the residual magnetic field with respect to the measurement magnetic field when the magnetic field reconstruction is performed with eigen-modes marked with a circle. This magnitude is a calculation error of 0.1 ppm or less in a usual MRI magnetic field, which can be ignored. Hereinafter, with this concept, magnetic field calculation is performed by selecting from the eigen-modes marked with a circle in FIG. 12. However, the low-order side is selected by the concept written next.

On the other hand, for an eigen-mode to select as a high order, as discussed above, in the case of Nm=6, the eigen-modes whose eigen value is smaller (right side) than this eigen value is selected. Accordingly, in the diagram, in the basic eigen-mode group 9, when Equation (4) is selected by selecting from the vicinity where the number 7 (109th in FIG. 11) is written to the vicinity of a 550th, high-order eigen-modes are selected.

Using the eigen-modes selected in this way, the current potential distribution is constructed and the magnetic field is calculated. The result of estimating and calculating the magnetic field distribution of only the high-order components in the magnetic field measurement position is shown in FIGS. 13A and 13B by the magnetic field contour lines.

The current potential distribution obtained here may be obtained by subtracting the sum of the eigen-modes from a first eigen-mode to the low-order eigen-mode in the vicinity of an 109th position from the result of the sum of the eigen-modes from the first eigen-mode to the eigen-mode in the vicinity of a 550th.

Figure 13A:
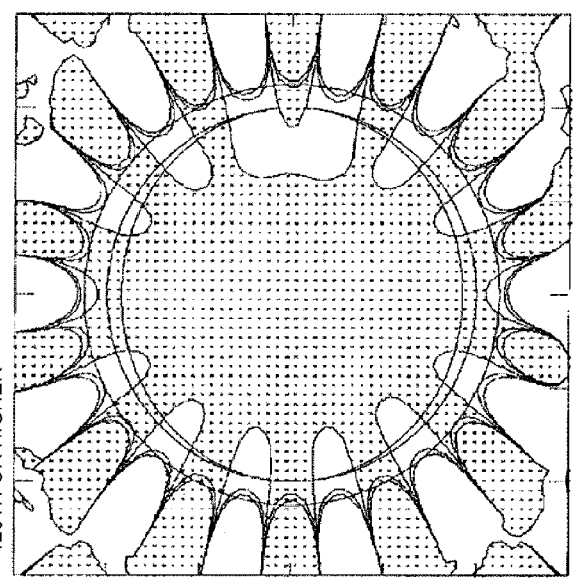
FIGS. 13A and 13B are a diagram of a magnetic field distribution obtained by performing magnetic field reconstruction with high-order eigen-mode components by the method according to the present invention.
Figure 13B:
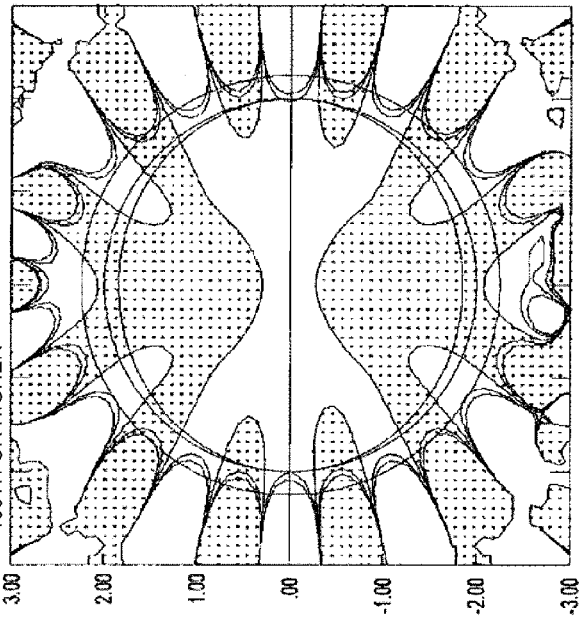

FIGS. 13A and 13B show a magnetic field distribution almost uniform in the circumferential direction. The hit point region is a low magnetic field region. This distribution reproduces the magnetic field design concept of FIGS. 4A and 4B, and it can be said that the distribution shows the validity of the previous discussion.

The contour lines illustrate the contour lines of the magnetic field intensity at zero and ±0.5 ppm equivalent (with respect to the final target magnetic field such as 1.5 T uniformity or $B^{3T}$). In addition, the lines also illustrate an ellipse of 50 cmφ, 40 cmφ, and 40 cm (X direction)-37 cm (Z direction). 50 cmφ, is a magnetic field measurement surface, others are magnetic field evaluation surfaces used for magnetic shimming. The center of these ellipses and circles is the center of the magnetic field measurement position. FIG. 13A is high-order eigen-modes including a seventh eigen-mode uniform in the circumferential direction, FIG. 13B is high-order components including an eighth eigen-mode uniform in the circumferential direction, not including the seventh. In FIGS. 13A and 13B, the eigen-mode numbers 100 and 120 or higher are selected by the eigen-mode number to reproduce the magnetic field distribution. Therefore, the number of unevenness in the circumferential direction of the magnetic field distribution is different in FIG. 13A and FIG. 13B. The hit point region is a region where the maximum static magnetic field is negative. In addition, FIG. 13A is the X-Z plane and FIG. 13B is a Y-Z plane.

When the magnetic field distributions shown in these diagrams with the circles and ellipses centered on the magnetic field measurement position are compared, in the Z direction, the magnetic field distributions and the circular shapes and elliptical shapes have high symmetry. However, it is understood that the magnetic field distribution contour lines enter inside the circular shapes and the elliptical shapes in the left side (Y<0) on the y-Z plane (FIG. 13B). That is, it can be understood that it is necessary to adjust the measurement position by moving the center of the magnetic field measurement position about 5 mm rightward (Y is a positive direction). Based on the magnetic field distributions reconstructed from the high-order components as described above, the sensor position evaluation unit 104 outputs information on whether or not the magnetic sensor position is appropriately arranged to the display unit 107 and presents the optimum sensor position to an operator.

FIG. 14 is a diagram showing the PP values of a residual magnetic field as a function of an amount of movement from an obtained magnetic field distribution in magnetic field calculation in a case where a magnetic field measurement center is moved in high-order eigen-modes. That is, FIG. 14 shows the result obtained by extracting the high-order eigen-modes from the measurement magnetic field of FIG. 10 and obtaining the PP value of the residual magnetic field component represented by addition of the high-order eigen-modes on the magnetic field measurement surface 8 while changing the center position of the magnetic sensor in the calculation. The PP value of the residual magnetic field is shown by changing the center position of the magnetic sensor in X, Y, and Z. In other words, in a case where the center of magnetic field measurement is moved in each of X, Y, Z directions, FIG. 14 visualizes the state of the deviation indicated by the magnetic field intensity distribution by the high-order eigen-modes on the magnetic field measurement surface 8. As shown in FIG. 13B, there are eigen-mode number 120 or higher, and eigen-modes of a seventh or lower symmetric in the circumferential direction are not included. From this diagram, the position in the X direction and the Z direction is at the position at which the residual magnetic field is the smallest, but as described in FIG. 13B, it is understood that moving in the Y direction by 5 mm results in a residual magnetic field with a small PP value. Because high-order components are not suitable for shimming, it is advantageous to evaluate the magnetic field centered on the position at which the residual magnetic field of the highest order decreases and shimming to obtain better uniformity.

In this way, by using the shimming method of the Example 1, it is possible to perform shimming with good uniformity.

Example 2

A second example will be described. In PTL 1, a magnetic field is measured on a magnetic field measurement surface such as a spherical surface or an ellipsoid, the measurement magnetic field is input as it is to a shimming code, and a magnetic material (an iron piece or the like), arrangement or the like is calculated. Here, the shimming code measures the magnetic field in a magnetic field utilization region (imaging region in MRI) and uses the magnetic field distribution data as an input. The shimming code is a code to calculate the position and amount of the magnetic material on the arrangement region where iron arrangement necessary for flattening (shimming) the input magnetic field distribution is predetermined.

In PTL 1, the magnetic field is evaluated at the magnetic field measurement position at the time of shimming. However, since the method invented this time can calculate the magnetic field at an arbitrary position (inside the virtual current plane 1) from the measurement magnetic field, it is possible to place the magnetic field measurement surface and the magnetic field evaluation surface at different positions.

In general, shimming improves the uniformity most at a position where the magnetic field is evaluated. Therefore, in order to obtain good uniformity in a narrow region from the center, it is better to make the surface on which the magnetic field is evaluated narrow. For example, it is assumed that the radius of the surface is 20 cm from the center of the apparatus.

On the other hand, it is desirable to measure a magnetic field over a wide range of the magnetic field measurement surface. This is because the high-order components included in the measurement magnetic field is more easily measured at a position far from the center. For an ordinary MRI apparatus, the magnitude of the measurement magnetic field plane is limited in order to avoid approaching a bore diameter of the central portion and the strong magnetic field existing for each coil block in the magnet, but the magnetic field measurement with the spherical surface with a diameter of about 50 cm is possible. Because there is no need to make the size of the imaging region a bigger spherical surface, it is considered that the radius 50 cm is appropriate here. In these cases, the magnetic field distribution of the magnet apparatus is measured on the surface of a sphere (DSV) with a diameter of 50 cm, and 40 cm DSV surface magnetic field evaluation and shimming will be performed. In this way, separately treating the magnetic field measurement surface and the magnetic field evaluation (adjustment) can be executed without any problem by the above-described shimming method of the present example, which could not be achieved by the invention of PTL 1.

The magnetic field measurement is performed with the tool shown in FIG. 9A, with a radius $R_i$ set to the axial position, $Z_i$ position (i=1 to Np) and rotated around the magnet axis (Z axis).

$$Xm = R_i \cos((k-1)2\pi/Nt)$$

$$Ym = R_i \sin((k-1)2\pi/Nt)$$

$$Zm = Z_i$$

m=(i−1)×Np+k, m indicates the total number of magnetic field measurement points. It is assumed that there are Np magnetic sensors, one R-Z plane is measured with Nt measured cross sections around the Z axis. The total number of magnetic field measurement points is NpNt.

$R_i$ and $Z_i$ are functions of the elevation angle $\varphi_i$ in the Z direction=(i−1) (an)/(Np−1)−α$\pi$/2 (i=1 to Np), wherein, $$R_i = R \sin(\varphi_i) \quad (10)$$

$$Z_i = R \cos(\varphi_i) \quad (11)$$

Here, α is about 0.9 to 0.999, and the exact value is determined on the basis of the detailed design of the magnetic field measuring machine. It is desired to widen the measurement position as wide as possible at a semicircular cross-sectional position, but on the spherical surface, near the axis, there is a region where the magnetic sensor cannot be arranged, so this region as α is removed and the magnetic sensor is arranged. Magnetic field measurement is performed on a radius R plane, and all magnetic sensors have the same spherical surface and R=25 cm. On the magnetic field evaluation surface used for shimming, an input position from Zm, Ym, and Zm to the shimming code is as follows.

$$Xm' = (0.2/0.25)Xm \quad (12)$$

$$Ym' = (0.2/0.25)Ym, \quad (13)$$

$$Zm' = (0.20/0.25)Zm, \quad (14)$$

At this position, a magnetic field is input to the shimming code, and the position is assumed to be a magnetic field evaluation point at the time of shimming. In other words, in the shimming system of the present example, the magnetic field extrapolation calculation unit 102 shown in FIG. 17 outputs a magnetic field distribution on a surface different from the magnetic field measurement surface to the shimming calculation unit 105 based on the magnetic field measurement result, and the shimming calculation unit 105 which received the information calculates the arrangement and quantity of the shim magnetic material (iron piece) such that the uniformity of the magnetic field on the surface satisfies a specification. The result calculated by the shimming code in this manner is shown in FIG. 15.

FIG. 15 is a diagram showing an example of a magnetic field distribution when a magnetic field distribution at a position of a radius of 20 cm is calculated by a magnetic field estimation calculation method of the present invention based on a magnetic field measured with a spherical surface having a radius of 25 cm. It is a magnetic field distribution similar to the magnetic field distribution (FIG. 10) measured on the surface with a radius of 25 cm, but the distribution is slightly smaller in amplitude. This is because the magnetic field distribution at the position of the radius of 20 cm is used, and both are in a proper relationship.

As described above, since an arbitrary magnetic field evaluation point can be used in the shimming method of the present example, magnetic field evaluation points and surfaces at the time of shimming do not depend on the measurement position and measurement surface. By using the magnetic field calculation method of the present example, it is possible to calculate the magnetic field at an arbitrary position in the region surrounded by the virtual current plane 1. Therefore, the magnetic field evaluation position can be selected regardless of the measurement position. As a selection condition of the magnetic field evaluation point, it is desirable that the magnetic field evaluation point is close to the region to be used after the magnetic-field-adjustment and the position rotated in the circumferential direction around the device axis is selected. The latter is because it is easy to extract eigen-modes uniform in the circumferential direction.

In Equations (12) to (14), the magnetic field evaluation point is determined solely by approaching the origin with reference to the magnetic field measurement point. However, this magnetic field evaluation point does not need to match the magnetic field measurement point, and may be an arbitrary point. In that sense, because increasing the number of magnetic field evaluation points more than that of the measurement points leads to the prevention of the local appearance of a large residual magnetic field, it can be said that it leads to better uniformity.

Example 3

FIG. 16 shows a shimming procedure according to the present invention, which is a combination of the above two examples. FIG. 16 is a flowchart showing a magnetic shimming process according to a third example of the present invention. As shown in the left diagram of FIG. 16, in the present example, prior to entering the shimming operation so far, the position of the magnetic sensor is adjusted by the high-order eigen-mode components according to the present invention. Specifically, in step S10, magnetic field measurement is performed, and in step S20, it is determined whether or not the measurement position is good. In a case where the measurement position of the magnetic field is not good in step S20, the position of the magnetic sensor is adjusted in step S30. At this time, even if the position of a magnetic field measurement supporting tool is inappropriate, it is also possible to perform the shimming by determining the magnetic field evaluation point separately from the magnetic sensor center position and the center position of the magnetic field evaluation point in the calculation.

In step S20 of the left diagram of FIG. 16, in a case where it is determined that the measurement position is good, the process proceeds to the right diagram of FIG. 16. In the right diagram of FIG. 16, the portion written as the shimming operation in step S70 is a general shimming operation including the shimming operation in PTL 1, but before that, the magnetic field distribution of the magnetic field evaluation surface is estimated and calculated by the method of the present invention, for example, the method of Example 1, and this magnetic field is used as a magnetic field input of the shimming operation. When the magnetic field measurement is performed in step S40 and the magnetic field distribution of the magnetic field evaluation surface is estimated and calculated in step S50, since not only the PP value of the residual magnetic field on the magnetic field evaluation surface but also the magnetic field inside the surface can be estimated, it is possible to calculate indices of the residual magnetic field such as magnetic field evaluation and volume root square mean in various aspects. In step S60, it is determined whether or not the uniformity of the magnetic field is good, that is, whether the magnetic field uniformity is good by comparing the indices with the specifications of the apparatus in general. As a result, if the uniformity is not sufficient and shimming is incomplete (No), the shimming operation in step S70 is repeated, and then, the magnetic field measurement in step S40 and the estimation calculation of the magnetic field distribution in step S50 are performed, and the process returns to the determination of uniformity. If the uniformity is good, the process proceeds to step S80, and the shimming operation is ended.

According to the shimming method of the present example described above, it is possible to accurately grasp the magnetic field distribution in other VOIs (magnetic field evaluation surface, same as the surface to be shimmed) in addition to the magnetic field measurement position. By applying this method, it is possible to perform shimming which can make uniformity better than the method of the related art.

As a result, it is possible to evaluate the magnetic field during shimming different from the magnetic field measurement surface. In addition, magnetic sensor position adjustment that reflects the internal coil block position can also be performed by position adjustment of the magnetic sensor position.

Furthermore, since the magnetic field evaluation surface and the magnetic field measurement position can be different, even in MRI apparatuses with different FOV specifications, different specifications, that is, even in the MRI apparatuses whose specifications of magnetic field evaluation surfaces are different and FOV magnitudes are also different, since the magnetic field measurement surface of the same magnitude can be used, it is possible to use the same magnetic field measurement instrument for multiple models. In this way, it is possible to greatly reduce the burden on the operator.

REFERENCE SIGNS LIST 1 virtual current plane
2 magnetic field evaluation surface
3 continuously arranged shim tray
4 imaging region (FOV)
5 shim pocket of discretely arranged shim tray
6 magnetic field PP value shown by eigen-mode upper limit function
7 magnetic field intensity contour
8 magnetic field measurement surface
9 number position of axisymmetric eigen-modes
10 MRI magnet
10f bore of MRI magnet
11 coil block of shield coil
12 coil block of main coil
13 coil block
15 eigen-mode (selected)
16 eigen-mode (not selected)
20 magnetic sensor support plate
21 coil block sectional surface current
22 examinee
23 bed
24 gradient magnetic field coil

The invention claimed is:

1. A shimming system comprising:
a magnetic field measurement device that has a sensor unit comprising a plurality of magnetic field sensors fixed to a rotating plate and can perform magnetic field measurement of a large number of magnetic field measurement points; and
a shim amount calculation unit that estimates a magnetic moment or current distribution that reproduces a magnetic field distribution obtained by the magnetic field measurement device on a predetermined closed surface, estimates a magnetic field distribution at an arbitrary point existing in the closed surface from the estimated magnetic moment or current distribution, and outputs a distribution of a shim magnetic material that generates an adjustment magnetic field for correcting the magnetic field distribution at the arbitrary point based on the estimated magnetic field distribution,
wherein the shim amount calculation unit virtually arranges a closed surface surrounding the magnetic field measurement points, obtains a response matrix about a magnetic field to the magnetic field measurement points from a current distribution or a magnetic moment per unit on the closed surface to the measured magnetic field by singular value decomposition, estimates a magnetic field distribution in the closed surface using obtained eigen-modes, extracts high-order eigen-mode components from the eigen-modes, and presents a position at which a residual magnetic field due to the high-order eigen-mode component is reduced as a position to move the center of the magnetic field measurement device.

2. The shimming system according to claim 1,
wherein the shim amount calculation unit arranges the closed surface as a region included in a measurement surface having the magnetic field measurement points on the surface thereof, estimates and calculates the magnetic moment or current distribution on the closed surface, and estimates and calculates a magnetic field at a point included in the measurement surface based on the estimated result.

3. The shimming system according to claim 1,
wherein a PP value of a residual magnetic field obtained by a function of a magnetic field intensity and an eigen-mode upper limit number is displayed in order to select the eigen-mode.

4. The shimming system according to claim 3,
wherein an axisymmetric eigen-mode number in superposition with the display of the PP value of the residual magnetic field obtained by the function of the magnetic field intensity and the eigen-mode upper limit number is displayed.

5. A shimming system comprising:
a magnetic field measurement device that has a sensor unit comprising a plurality of magnetic field sensors fixed to a rotating plate and can perform magnetic field measurement of a large number of magnetic field measurement points; and
a shim amount calculation unit that estimates a magnetic moment or current distribution that reproduces a magnetic field distribution obtained by the magnetic field measurement device on a predetermined closed surface, estimates a magnetic field distribution at an arbitrary point existing in the closed surface from the estimated magnetic moment or current distribution, and outputs a distribution of a shim magnetic material that generates an adjustment magnetic field for correcting the magnetic field distribution at the arbitrary point based on the estimated magnetic field distribution,
wherein the shim amount calculation unit arranges a current distribution or a magnetic moment per unit on a closed surface including the magnetic field measurement points, obtains a response matrix about a magnetic field to the magnetic field measurement points from a current distribution or a magnetic moment per unit on the closed surface to the measured magnetic field by singular value decomposition, and estimates a magnetic field distribution in the closed surface using obtained eigen-modes.

6. The shimming system according to claim 5,
wherein the shim amount calculation unit presents a relationship between a movement distance of a center position of the magnetic field measurement device and a residual magnetic field PP value of a magnetic field component according to high-order eigen-modes from the eigen-modes.

7. The shimming system according to claim 5,
wherein the shim amount calculation unit adjusts a position of the sensor at the time of starting a shimming operation after the magnetic field measurement adjustment and virtually arranges a closed surface surrounding the magnetic field measurement points, obtains a response matrix about a magnetic field to the magnetic field measurement points from a current distribution or a magnetic moment per unit on the closed surface to the measured magnetic field by singular value decomposition, estimates a magnetic field distribution in the closed surface using the obtained eigen-modes, extracts high-order eigen-mode components from the eigen-modes, presents a position at which a residual magnetic field due to the high-order eigen-mode components is reduced as a position to move the center of the magnetic field measurement device, and estimates and calculates a magnetic field input value to a shimming code.

8. The shimming system according to claim 7,
wherein a PP value of a residual magnetic field obtained by a function of a magnetic field intensity and an eigen-mode upper limit number is displayed in order to select the eigen-mode.

9. The shimming system according to claim 8,
wherein an axisymmetric eigen-mode number in superposition with the display of the PP value of the residual magnetic field obtained by the function of the magnetic field intensity and the eigen-mode upper limit number is displayed.

10. The shimming system according to claim 5,
wherein a PP value of a residual magnetic field obtained by a function of a magnetic field intensity and an eigen-mode upper limit number is displayed in order to select the eigen-mode.

11. The shimming system according to claim 10,
wherein an axisymmetric eigen-mode number in superposition with the display of the PP value of the residual magnetic field obtained by the function of the magnetic field intensity and the eigen-mode upper limit number is displayed.

* * * * *